United States Patent
Ramirez et al.

(10) Patent No.: US 11,389,409 B2
(45) Date of Patent: Jul. 19, 2022

(54) TRANSDERMAL DEVICE COMPRISING ACETAMINOPHEN PRODRUG

(71) Applicant: Remedy Diagnostics LLC, Dallas, TX (US)

(72) Inventors: Lori Ramirez, Dallas, TX (US); Reza Amirzadeh, Dallas, TX (US); Opinya Ekabo, Dallas, TX (US)

(73) Assignee: REMEDY DIAGNOSTICS LLC, Dallas, TX (US)

( * ) Notice: Subject to any disclaimer, the term of this patent is extended or adjusted under 35 U.S.C. 154(b) by 0 days.

(21) Appl. No.: 17/005,901

(22) Filed: Aug. 28, 2020

(65) Prior Publication Data

US 2021/0059957 A1 Mar. 4, 2021

Related U.S. Application Data

(60) Provisional application No. 62/894,020, filed on Aug. 30, 2019.

(51) Int. Cl.
*A61K 9/70* (2006.01)
*A61K 47/32* (2006.01)
*A61K 47/10* (2017.01)
*A61K 31/222* (2006.01)

(52) U.S. Cl.
CPC .......... *A61K 9/7084* (2013.01); *A61K 31/222* (2013.01); *A61K 47/10* (2013.01); *A61K 47/32* (2013.01)

(58) Field of Classification Search
None
See application file for complete search history.

(56) References Cited

U.S. PATENT DOCUMENTS

| 6,024,976 | A | 2/2000 | Miranda et al. | |
|---|---|---|---|---|
| 7,244,447 | B2 * | 7/2007 | Hsu | A61K 9/0014 424/443 |
| 9,809,557 | B2 | 11/2017 | Larsen et al. | |
| 2003/0118528 | A1 * | 6/2003 | Walters | A61K 47/55 424/59 |
| 2010/0172960 | A1 * | 7/2010 | Yu | A61P 1/00 424/449 |
| 2011/0014285 | A1 * | 1/2011 | Herzenberg | A61K 9/0019 424/474 |

(Continued)

FOREIGN PATENT DOCUMENTS

WO WO 2008/029200 A1 3/2008
WO WO 2008/060506 A2 5/2008

OTHER PUBLICATIONS

By Lee et al. "Novel immediate/sustained-release formulation of acetaminophen-ibuprofen combination (Paxerol®) for severe nocturia associated with overactive bladder: A multi-center, randomized, double blinded, placebo-controlled, 4-arm trial", Neurology and Urodynamics, Feb. 2019, vol. 38, Issue 2 (Year: 2019).*

(Continued)

*Primary Examiner* — Isis A Ghali
(74) *Attorney, Agent, or Firm* — Foley & Lardner LLP

(57) ABSTRACT

The present invention relates to transdermal devices comprising prodrugs of anti-pyretic, analgesic, or anti-inflammatory molecules, methods of making such devices, and methods of use thereof for treating, preventing, minimizing, and/or diminishing fever or pain.

7 Claims, 9 Drawing Sheets

(56) References Cited

U.S. PATENT DOCUMENTS

| | | | | |
|---|---|---|---|---|
| 2011/0212926 A1* | 9/2011 | Muhammad | ............ | A61P 43/00 |
| | | | | 514/119 |
| 2011/0263545 A1* | 10/2011 | Muhammad | ......... | A61K 31/195 |
| | | | | 514/161 |
| 2015/0056192 A1* | 2/2015 | Chaturvedi | .......... | A61K 31/475 |
| | | | | 424/133.1 |
| 2017/0035891 A1 | 2/2017 | Karp et al. | | |

OTHER PUBLICATIONS

Kevin, "Prodrug for transdermal drug delivery-trends and challenges", Journal of Drug Targeting, vol. 24, No. 8, 671-678, (Year: 2016).*

Thomas et al., "soft alkyl ether prodrugs of a model phenolic drugs: The effect of incorporation of ethyleneoxy group on transdermal delivery", Molecules, 14, 4231-4245. (Year: 2009).*

Thompson "Investigating the fundamental of drug crystals growth using atomic force microscopy", Thesis submitted to the university of Nottingham, May (Year: 2003).*

IKM Morton et al., Concise Dictionary of Pharmacological Agents (Year: 1999).*

International Search Report and Written Opinion issued in co-pending International Patent Application No. PCT/US2020/048395, dated Dec. 7, 2020.

Abualhasan, et al., "Synthesis and Formulation of Ibuprofen Pro-Drugs for Enhanced Transdermal Absorption," *Intern. Journ. of Pharmacy and Pharmaceutical Sciences*, vol. 7, No. 2, pp. 352-354 (2015).

\* cited by examiner

TRANSDERMAL DEVICE COMPRISING ACETAMINOPHEN PRODRUG

CROSS-REFERENCE TO RELATED APPLICATIONS

This application claims the priority benefit under 35 USC § 119 to U.S. provisional Application No. 62/894,020, filed Aug. 30, 2019, the entire contents of which is incorporated herein by reference in its entirety.

FIELD OF THE INVENTION

The present invention relates to transdermal drug delivery systems for the delivery of anti-pyretic, analgesic, or anti-inflammatory drugs and methods of making and using the same. More particularly, the present invention relates to transdermal drug delivery systems for the delivery of prodrugs of commonly used drugs such as acetaminophen and ibuprofen.

BACKGROUND

Anti-pyretic, analgesic, and anti-inflammatory drugs such as acetaminophen (paracetamol, APAP) and ibuprofen (IBU) are among the most commonly used medications, including in infants and children. Oral administration in liquid and tablet or capsule forms is the most common route of delivery for these drugs. However, oral administration of these drugs, especially in pediatric populations but also in non-pediatric patient populations such as in elderly patients, is not always possible or practical. For example, patients with vomiting or diarrhea may be unable to take or retain an oral dose of acetaminophen or ibuprofen. Uncooperative patients may also often refuse to take an oral dose of the drugs due to taste, fear, or other reasons. Accordingly, an alternative route of administration, such as transdermal delivery, may be more suitable for delivering these drugs in such patient populations.

Transdermal delivery of drugs has several advantages such as avoiding problems with gastrointestinal drug absorption (due to pH, enzymatic activity, drug-food interactions, etc.), elimination of variation in plasma concentration after gastrointestinal absorption, bypassing hepatic first pass metabolism and thus reducing potential for hepatic injury, avoiding adverse gastrointestinal reactions, and an ability to tailor the treatment for individual use by a quick interruption or cessation of treatment.

However, due to the barrier function of the skin, problems exist with transdermal delivery of commonly used anti-pyretic, analgesic, and anti-inflammatory drugs. Not all drugs can be formulated into dosage forms suitable for transdermal delivery. For example, the physicochemical properties of acetaminophen and ibuprofen are not particularly well-suited for transdermal delivery. Thus, there is a need in the art for safe and effective transdermal devices and pharmaceutical compositions capable of transdermally delivering therapeutically effective doses of anti-pyretic, analgesic, and anti-inflammatory molecules. The present invention describes such transdermal drug delivery devices and compositions.

SUMMARY

In one aspect, a transdermal drug delivery system for topical application is provided, the system comprising (a) an adhesive polymer matrix layer; and (b) at least one stable NSAID or analgesic prodrug dispersed within the polymer matrix layer.

In some embodiments, the analgesic prodrug is an acetaminophen prodrug having the structure of formula I:

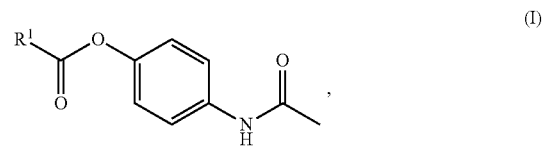

wherein $R^1$ is optionally substituted $C_1$-$C_6$ alkyl.

In some embodiments, the NSAID prodrug is an ibuprofen prodrug having the structure of formula II:

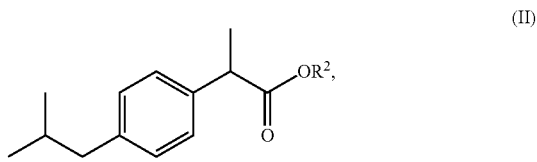

wherein $R^2$ is optionally substituted $C_1$-$C_6$ alkyl.

In some embodiments, $R^1$ is methyl. In some embodiments, $R^2$ is ethyl. In some embodiments, the prodrug is chemically and physically stable. In some embodiments, the prodrug is chemically and physically stable over a period of time selected from the group consisting of about 3 months, about 6 months, about 9 months, about 1 year, about 1.5 years, about 2 years, about 2.5 years, and about 3 years.

In some embodiments, upon topical application to the skin or mucosa of a subject in need (a) the system releases a therapeutically effective amount of the prodrug over a desired period of time; and/or (b) the prodrug diffuses through the skin or mucosa of the subject to achieve desired therapeutic systemic levels of the analgesic or NSAID.

In some embodiments, the transdermal drug delivery system further comprises (a) a backing layer; (b) a release liner; (c) a rate-controlling polymeric membrane; or (d) any combination of (a), (b), and (c).

In some embodiments, the adhesive polymer matrix comprises (a) a pressure-sensitive adhesive; (b) an acrylic polymer; (c) a polymer in which the prodrug is soluble; or (d) any combination of (a), (b) and/or (c).

In some embodiments, the adhesive polymer matrix comprises (a) from about 200 mg to about 1,000 mg of the prodrug; (b) from about 1,000 mg to about 2,550 mg the prodrug; or (c) a prodrug concentration of about 250 mg/cm³ to about 1,250 mg/cm³.

In some embodiments, the adhesive polymer matrix comprises a combination of an acetaminophen prodrug and an ibuprofen prodrug.

In some embodiments, the transdermal drug delivery system further comprises at least one pharmaceutically acceptable permeation enhancer and/or penetration enhancer. In some embodiments, the permeation enhancer or penetration enhancer is selected from the group consisting of (1) an alcohol, polyhydric alcohol, or glycol such as dipropylene glycol, propylene glycol, butylene glycol, polyethylene glycol, and oleyl alcohol; (2) oils such as olive oil, squalene, and lanolin; (3) fatty ethers such as cetyl ether and oleyl ether; (4) fatty acid esters such as isopropyl myristate;

(5) urea and urea derivatives such as allantoin; (5) polar solvents such as dimethyidecylphosphoxide, methyloctylsulfoxide, dimethyllaurylamide, dodecylpyrrolidone, isosorbitol, dimethylacetonide, dimethylsulfoxide (DMSO), decylmethylsulfoxide, and dimethylformamide; (6) salicylic acid; (8) amino acids; (9) benzyl nicotinate; (10) higher molecular weight aliphatic surfactants such as lauryl sulfate salts; (11) acids such as oleic acids, linoleic acids, and ascorbic acid; and (12) panthenol, butylated hydroxytoluene, tocopherol, tocopheryl acetate, tocopheryl linoleate, propyl oleate, and isopropyl palmitate; and (13) any combination thereof. In some embodiments, the polyethylene glycol is PEG400 and the alcohol is ethanol.

In some embodiments, the delivery system delivers a therapeutically effective amount of the prodrug over a period of time selected from the group consisting of (a) about 4 to about 30 hours, or any amount of time in-between these two values; (b) about 8 to about 24 hours; (c) about 12 to about 24 hours; (d) about 4 to about 8 hours; or (e) about 8 to about 16 hours.

In some embodiments, the delivery system has a skin or mucosa contact region area of from about 1 to about 20 cm$^2$, about 5 to about 15 cm$^2$, about 7 to about 13 cm$^2$, or about 9 to about 12 cm$^2$.

In one aspect, a method of treating pain in a subject in need is provided, the method comprising applying a transdermal drug delivery system according to any embodiment herein to the skin or mucosa of the subject.

In some embodiments, the subject is a human. In some embodiments, the subject is (a) a newborn or infant between the age of about 0 to about 1 year; (b) a child between the age of about 1 to about 3 years; (c) a child between the age of about 3 to about 6 years; (d) a child between the age of about 6 to about 12 years; (e) a child between the age of about 12 to about 18 years; (f) less than 21 years of age; or (g) an adult 21 years of age or older.

In some embodiments, the subject is nauseous, has diarrhea, or is vomiting. In some embodiments, the subject has difficulty swallowing. In some embodiments, the subject is unable to ingest a complete oral NSAID or analgesic dose recommended for the subject's age and weight.

In some embodiments, the subject has a fever, headache, backache, arthritic pain, toothache, premenstrual or menstrual cramps, the common cold, musculoskeletal pain, neuropathic pain, chronic pain, connective tissue pain, or pain associated with injury.

In some embodiments, the transdermal drug delivery system is applied to the skin of the chest, upper arm, hip, back, abdomen, buttock, upper torso, flank, shoulder, or thigh of the subject.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION

I. Overview of the Invention

Figure 1:
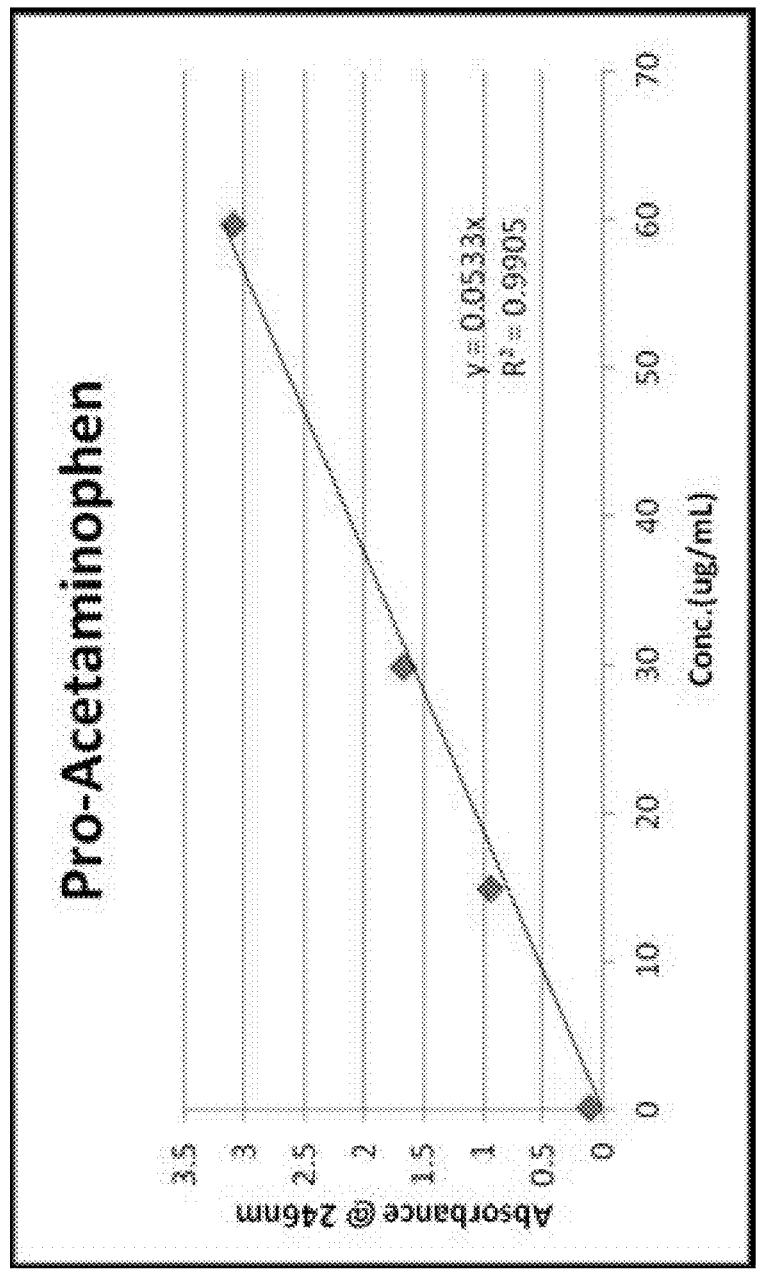
FIG. 1 shows the calibration of a UV-Vis spectrometer for use in determining the concentration of 4-acetoxyacetanilide by detecting absorbance at 246 nm.

The present invention provides transdermal drug delivery systems (e.g., transdermal patches) for the systemic delivery of anti-pyretic, analgesic, or anti-inflammatory prodrugs. A prodrug refers to an inactive precursor of a drug molecule that is enzymatically or chemically converted in vivo to release the pharmacologically active drug molecule. Parameters to be considered in determining the suitability of a molecule for transdermal delivery include solubility, stability, and delivery of a therapeutic amount of drug at a suitable delivery rate over the duration of use. The transdermal drug delivery systems (e.g., transdermal patches) of the present invention comprise prodrugs of anti-pyretic, analgesic, or anti-inflammatory drugs.

The formulations comprising the prodrug molecules described herein have improved physicochemical and pharmacokinetic features for transdermal delivery as compared to the active drug molecules themselves. Prior to the present invention, it was thought that the prodrugs encompassed by the invention would not be stable in a transdermal delivery system. Thus, the successful development of a transdermal delivery system for anti-pyretic, analgesic, or anti-inflammatory drugs was unexpected and surprising.

The delivery of the prodrug rather than the active form of the drug offers the advantage of reduced toxicity (e.g., hepatoxicity in the case of APAP) since the prodrug is inactive and the active form of the drug is delivered slowly via metabolization or hydrolysis of the prodrug rather than a flush delivery of active drug, which is characteristic of oral dosing of an active drug. Here, controlled release is accomplished by combining the gradual release of the transdermal system with the gradual release of active drug achieved via the gradual conversion of prodrug to active drug. Transdermal drug delivery especially improves patient compliance in uncooperative patients, which are often opposed to taking medicine orally, rectally, or via injection.

The transdermal drug delivery systems (e.g., transdermal patches) of the present invention are useful for treating and/or preventing any therapeutic indication associated with the active form of the prodrug, such as but not limited to pain, fever, and/or inflammation. The method comprises applying a transdermal drug delivery system (e.g., a transdermal patch) of the invention to the skin of a subject in need thereof. In a particular aspect, the transdermal drug delivery systems of the invention are useful in methods of treating patients. The transdermal delivery systems (e.g., transdermal patches) of the invention may be particularly useful for patients who have vomiting or diarrhea, or are unconscious, or who refuse to take an oral dose of drugs because of taste, pain or fear of swallowing, or other reasons. In addition to an anti-pyretic, analgesic, or anti-inflammatory prodrug, one or more other additional active agents may also be incorporated into the transdermal drug delivery systems.

As detailed in the Examples below, exemplary prodrug molecules corresponding to acetaminophen and ibuprofen were assessed for solubility at concentrations sufficient for therapeutic efficacy as well as stability in a model solvent/vehicle to determine their suitability for use in a transdermal drug delivery system. The prodrug formulations were further tested for skin permeation across human skin. It was surprisingly discovered that the prodrug formulations exhibited excellent prodrug solubility, stability, and permeation across the skin. Thus, the prodrug formulations of the invention are suitable for transdermal delivery (e.g., in transdermal patches) of commonly used anti-pyretic, analgesic, and anti-inflammatory drugs such as acetaminophen and ibuprofen. The prodrug formulations of the invention may be incorporated into any pharmaceutically acceptable transdermal delivery dosage form (e.g., transdermal patch) which can be applied to the skin of a subject in need thereof.

Oral administration is the most common route of delivery of anti-pyretic, analgesic, and anti-inflammatory drugs. In addition to issues with patient compliance, especially in uncooperative patients, which may be pediatric patients, oral delivery of commonly used anti-pyretic, analgesic, and anti-inflammatory drugs is associated with undesirable side effects such as hepatotoxicity or gastrointestinal toxicity. For example, oral delivery of ibuprofen can irritate the lining of the stomach and is generally contraindicated in people with ulcers or upper GI tract irritation.

The transdermal drug delivery systems of the invention provide a number of potential benefits over conventional dosing regimens. The benefits include avoiding problems with gastrointestinal drug absorption (due to pH, enzymatic activity, drug-food interactions, etc.), elimination of variation in plasma concentration after gastrointestinal absorption, bypassing hepatic first pass metabolism and thus reducing potential for hepatic injury, avoiding adverse gastrointestinal reactions, and an ability to tailor the treatment for individual use by quickly interrupting or stopping treatment.

In one aspect of the invention, a transdermal drug delivery system (e.g., transdermal patch) of the invention exhibits greater prodrug (e.g., an anti-pyretic, analgesic, or anti-inflammatory prodrug) absorption across the skin (and thus greater delivery of the active form of the drug) as compared to a transdermal drug delivery system of the active form of the drug. For example, in one embodiment, a transdermal drug delivery system of the invention exhibits an increase in transdermal prodrug absorption, as compared to the active form of the drug, of at least about 10%, at least about 15%, at least about 25%, at least about 30%, at least about 35%, at least about 40%, at least about 45%, or at least about 50%. In another embodiment, a transdermal drug delivery system of the invention exhibits an increase in transdermal prodrug absorption, as compared to the active form of the drug, of about 5%, about 10%, about 15%, about 25%, about 30%, about 35%, about 40%, about 45%, or about 50%.

The transdermal drug delivery systems (e.g., transdermal patches) of the invention are stable for a period of time of about 6 months, about 1 year, about 18 months, about 2 years, about 2.5 years, about 3 years, about 3.5 years, or about 4 years. In another embodiment, the transdermal drug delivery systems of the invention exhibit a minimum shelf life of about 1 year. In another embodiment, the transdermal drug delivery systems of the invention exhibit a minimum shelf life of about 2 years.

II. Transdermal Drug Delivery Systems

One aspect of the present invention is directed to a transdermal drug delivery system comprising an anti-pyretic, analgesic, or anti-inflammatory prodrug. A transdermal drug delivery system refers to a system (e.g., a transdermal patch) comprising a composition that releases an anti-pyretic, analgesic, or anti-inflammatory prodrug (which is subsequently processed into the active form of the drug) upon application to the skin or mucosa.

A transdermal drug delivery system (e.g., a transdermal patch) of the present invention generally comprises a backing layer, a prodrug-comprising layer, and, optionally, a release liner layer. The transdermal drug delivery system may be a substantially non-aqueous, solid form, capable of conforming to the surface with which it comes into contact (e.g., the subject's skin at the site of application), capable of maintaining contact without an adverse physiological response, and without being appreciably decomposed by aqueous contact during topical application to a subject. Many such systems, such as transdermal delivery patches, are known in the art and commercially available. The prodrug formulations of the invention may be incorporated into suitable known and/or commercially available patches.

The backing layer is generally impermeable to the prodrug, and any carriers, excipients, or one or more additional active ingredients that may be present and provides support and protection for the transdermal drug delivery system. The backing layer protects the pro-drug comprising layer and other layers from the environment and prevents the release/loss of the prodrug and other components to the environment prior to and during use. The backing layer may be of the same size or essentially of the same size as the prodrug-comprising layer. The backing layer can be of any appropriate thickness required for providing the desired support and protective functions. In some embodiments, a suitable thickness for the backing layer is from about 5 µm to about 300 µm. In some embodiments, the backing layer may be from about 5 to about 50 µm, from about 10 to about 50 µm, from about 50 to about 100 µm, from about 100 to about 150 µm, from about 150 to about 200 µm, from about 200 to about 250 µm, from about 250 to about 300 µm, from about 300 to about 400 µm, from about 400 to about 500 µm, from about 500 to about 600 µm, from about 600 to about 700 µm, from about 700 to about 800 µm, from about 800 to about 900 µm, or from about 900 to about 1000 µm thick.

Materials suitable for use as backing layers are well-known known in the art. Suitable materials for the backing layer may comprise films of acrylate, acrylonitrile-butadiene-styrene, acrylonitrile (methyl methacrylate) copolymer, acrylonitrile copolymer, ethylene ethyl acrylate, ethylene methyl acrylate, ethylene vinyl acetate, ethylene vinyl acetate copolymer, ethylene vinyl alcohol polymer, ionomers, nylon (polyamide), nylon (polyamide) copolymer, polybutylene, polycarbonate, polyester, polyethylene terephthalate, thermoplastic polyester copolymer, polyethylene copolymer (high density), polyethylene (high-molecularweight, high density), polyethylene (intermediate-molecular weight, high density), polyethylene (linear, low density), polyethylene (low density), polyethylene (medium density), polyethylene oxide, polyimide, polypropylene, polypropylene (coated), polypropylene (oriented), polystyrene, polyurethane, polyvinyl acetate, polyvinyl chloride, polyvinylidene chloride and/or styrene-acrylonitrile, metal foils, non-woven fabric, or cloth, or combinations thereof. In some embodiments, films may be metallized or pigmented. In some embodiments, the materials used for the manufacturing the backing layer include polyurethane, ethylene vinyl alcohol polymer, polyester, or combinations thereof.

On the side of the prodrug-comprising layer opposite to the backing layer, a release liner may be present. A release liner protects the adhesive layer (in some embodiments, the adhesive layer is also be the prodrug-comprising layer), which facilitates the attachment of the transdermal drug delivery system to the skin of the subject. The release liner is removed prior to application of the transdermal drug delivery system to the skin of the subject to expose the adhesive layer. The release liner may be a peelable release liner. Materials suitable for use as release liners are well-known known in the art and include the commercially available products of Dow Corning Corporation designated Bio-Release™ liner and Syl-Off™ 7610 and 3M's 1022 Scotch Pak. Materials suitable for the release liner also include, but are not limited to, polyester, polyethylene, polypropylene, polysiloxane, e.g. with a fluorosiliconized coating, polyacrylate, ethylene vinyl acetate, polyurethane, polyisobutene, or paper, or a combination thereof. In some embodiments, the paper is coated with silicone and/or polyethylene. In some embodiments, a foil consisting of polyethylene terephthalate may be used. In a further embodiment, one side of such foil may be siliconized. In some embodiments, a combination of any of the above materials may be used in the preparation of the release liner. The release liner may be of any appropriate thickness required for its protective function. In some embodiments, the release liner may be from about 2 to about 30 μm, from about 30 to about 50 μm, from about 50 to about 100 μm, from about 50 to about 60 μm, from about 60 to about 70 μm, from about 70 μm to about 80 μm, from about 80 μm to about 90 μm, or from about 90 μm to about 100 μm thick. In some embodiments, the release liner may further comprise a suitable adhesive.

In some embodiments, the transdermal drug delivery system includes one or more additional layers, such as one or more additional polymer matrix layers, or one or more adhesive layers that adhere the transdermal drug delivery system to the user's skin, such as a face adhesive layer. In other embodiments, the transdermal drug delivery system is monolithic, meaning that it comprises a single polymer matrix layer comprising a pressure-sensitive adhesive or bioadhesive with drug dissolved or dispersed therein, and no face adhesive, no rate-controlling membrane, no other polymeric adhesive layer and no other drug-containing layer. As used herein, a "monolithic" transdermal drug delivery system may include a backing layer and/or release liner and may be provided in a package.

A transdermal drug delivery system may include a drug impermeable backing layer or film. "Impermeable" to the drug intends that no substantial amount of drug loss through the backing layer is observed. The backing layer protects the polymer matrix from the environment and prevents loss of the drug and/or release of other components to the environment during use. Materials suitable for use as backing layers are well-known in the art and commercially available, such as films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1,000 micrometers. For example, 3M's Scotch Pak™ 1012 or 9732 (a polyester film with an ethylene vinyl acetate copolymer heat seal layer), 9723 (a laminate of polyethylene and polyester), or CoTran 9720 (a polyethylene film) are useful in the transdermal drug delivery systems described herein, as are Dow® backing layer films, such as Dow® BLF 2550 (a multi-layer backing comprising ethylene vinyl acetate layers and an internal vinylidene chloride/methyl acrylate layer).

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include silicone- or fluorocarbon-coated polyester release liners, such as the commercially available products of Dow Corning Corporation designated Bio-Release® liner and Syl-off® 7610, Loparex's PET release liner (silicone-coated) and 3M's 1020, 1022, 9741, 9744, 9748, 9749 and 9755 Scotchpak™ (fluoropolymer-coated polyester films). A polymer is an "adhesive" if it has the properties of an adhesive per se, or if it functions as an adhesive by the addition of tackifiers, plasticizers, crosslinking agents or other additives. The polymer matrix also may comprise tackifiers, plasticizers, crosslinking agents or other additives described herein. U.S. Pat. No. 6,024,976 describes polymer blends that are useful in accordance with the transdermal systems described herein. The entire contents of U.S. Pat. No. 6,024,976 are incorporated herein by reference.

A pressure-sensitive adhesive generally refers to a viscoelastic material which adheres instantaneously to substrates upon the application of light pressure and remains permanently tacky. A pressure-sensitive adhesive can serve as a carrier for the prodrug, control the release of the prodrug from the polymer matrix, as well as adhere the transdermal drug delivery system to the skin of the subject. A polymer is a pressure-sensitive adhesive when it has the properties of a pressure-sensitive adhesive per se or when it functions as a pressure-sensitive adhesive upon mixture with tackifiers, plasticizers or other additives. Generally, tackifiers are additives which differ other than in molecular weight from the polymers to which they are added. Any suitable pressure-sensitive adhesive that is biocompatible and is physically and chemically compatible with a prodrug of the invention may be used in an amount/thickness required to confer sufficient cohesion of the components of the drug delivery systems and adhesion to the skin of the subject. Parameters to be considered in the selection of a suitable pressure-sensitive adhesive include, stability, prodrug compatibility, prodrug solubility, solvent compatibility, etc.

The pressure-sensitive adhesive may include mixtures of different polymers. In some embodiments, the pressure-sensitive adhesive is a blend of polyisobutylenes (PIB) of different molecular weights. In some embodiments, the pressure-sensitive adhesive is a blend of high- and medium-molecular-weight PIBs. In some further embodiments, the pressure-sensitive adhesive further comprises low-molecular weight PIBs. In some embodiments, the pressure-sensitive adhesive is a rubber-based pressure sensitive adhesive that contains at least one natural or synthetic elastomeric polymer. In some embodiments, the pressure-sensitive adhesive is acrylic-based, i.e., the pressure-sensitive adhesive may comprise an acrylic polymer. Commonly used monomers for preparing acrylic-based pressure-sensitive adhesives include butyl acrylate, isobutyl acrylate, 2-ethyl hexyl acrylate, ethyl acrylate, methyl methacrylate, vinyl acetate, styrene, and acrylonitrile. In some embodiments, the pressure-sensitive adhesive is silicon-based, i.e., the pressure-sensitive adhesive may comprise a silicone polymer. In some embodiments, the pressure sensitive adhesive is a combination of acrylic and silicone polymers. In some embodiments, the pressure-sensitive adhesive comprises polyvinylpyrrolidone (PVP), poly(methyl methacrylate)s, or mixtures thereof. In some embodiments, the PVP is soluble PVP. Soluble PVP means that the polymer is soluble in water and generally is not substantially cross-linked, and has a molecular weight of less than about 2,000,000. PVP may refer to a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known under a variety of designations including Povidone, Polyvidone, Polyvidonum, Polyvidonum soluble, and Poly (1-vinyl-2-pyrrolidone). The copolymer vinyl acetate vinylpyrrolidone is known as Copolyvidon, Copolyvidone, and Copolyvidonum. See, generally, Buhler, Kollidon®: Polyvinylpyrrolidone for the Pharmaceutical Industry, BASF Aktiengesellschaft (1992). In some embodiments, the pressure-sensitive adhesive may be a hydrocolloid matrix, that is a material with a large water content that acquires adhesive properties a result of the moisture content. The pressure-sensitive adhesive may be a mixture of any of the materials described herein.

In some embodiments, the polymer matrix is a pressure-sensitive adhesive at room temperature and also has other desirable characteristics for use as an adhesive in a transdermal drug delivery system. Such characteristics include good adherence to skin without causing substantial irritation, ability to be peeled or otherwise removed without substantial trauma to the skin, ability to be removed without leaving behind a residue, retention of tack with aging, etc. In some embodiments, the polymer matrix has a glass transition temperature ($T_g$), measured using a differential scanning calorimeter, of between about −70° C. and 100° C. In some embodiments, the polymer matrix has a glass transition temperature ($T_g$), measured using a differential scanning calorimeter, of between about −70° C. and 0° C.

A transdermal drug delivery system may be packaged or provided in a package, such as a pouchstock material used for transdermal drug delivery systems in general. For example, DuPont's Surlyn® can be used in a pouchstock material. Alternatively, a pouchstock comprising a coextruded ethylene acrylic acid/low-density polyethylene (EAA/LDPE) material, or Barex from INEOS (acrylonitrile-methyl acrylate) may be used.

The concentration by weight of the prodrugs in the transdermal delivery system is generally about 1% to about 50%, about 1% to about 40%, about 3% to about 30%, about 5% to about 40%, about 1% to about 10%, about 10% to about 20%, about 20% to about 30%, about 30% to about 40%, or about 40% to about 50% by weight, or a range between and including any two of these values, all based on the total weight of the adhesive polymer matrix.

In some embodiments, the prodrug is an acetaminophen prodrug (e.g., 4-acetoxyacetanilide). In some embodiments, the prodrug is an ibuprofen prodrug (e.g., ethyl 2-(4-isobutylphenyl)-propanoate). Irrespective of whether there is high-loading or low-loading of the prodrug into the transdermal drug delivery system, the adhesive layer (e.g., comprising a pressure-sensitive adhesive) can be formulated to maintain acceptable shear, tack, and peel adhesive properties.

In some embodiments, the prodrug-containing layer is a polymer matrix that is non-adhesive. The transdermal drug delivery system may comprise a separate adhesive layer that adheres the transdermal drug delivery system to the skin of a subject. In certain embodiments, the transdermal drug delivery system comprises 1) a backing layer, 2) a non-adhesive polymer matrix layer comprising an anti-pyretic, analgesic, or anti-inflammatory prodrug, which defines an active surface area, 3) an adhesive layer, 4) and, optionally, 3) a release liner layer.

In some embodiments, the prodrug-comprising layer is a liquid or gel reservoir and the prodrug is dissolved or dispersed within the layer. In certain embodiments, the transdermal drug delivery system comprises (1) a backing layer, (2) a liquid or gel reservoir comprising an anti-pyretic, analgesic, or anti-inflammatory prodrug, (3) an adhesive layer, and, optionally, (4) a release liner layer. In some embodiments, transdermal drug delivery system further comprises a rate-controlling membrane.

In some embodiments the transdermal drug delivery system comprises a skin contacting face and an outward face. In some embodiments the skin contacting face has an active surface area of about 2 to about 3 $cm^2$, about 3 to about 4 $cm^2$, about 4 to about 5 $cm^2$, about 5 to about 6 $cm^2$, about 6 to about 7 $cm^2$, about 7 to about 8 $cm^2$, about 8 to about 9 $cm^2$, about 9 to about 10 $cm^2$, about 10 to about 11 $cm^2$, about 11 to about 12 $cm^2$, about 12 to about 13 $cm^2$, about 13 to about 14 $cm^2$, about 14 to about 15 $cm^2$, about 15 to about 16 $cm^2$, about 16 to about 17 $cm^2$, about 17 to about 18 $cm^2$, about 18 to about 19 $cm^2$, or about 19 to about 20 $cm^2$.

A. Prodrugs

The transdermal drug delivery systems of the present invention comprise at least one prodrug, or a pharmaceutically acceptable salt thereof, chemical analog, and/or derivative of the prodrug, of anti-pyretic, analgesic, or anti-inflammatory drugs. Examples of anti-pyretic, analgesic, or anti-inflammatory drugs include but are not limited to acetaminophen and NSAIDs such as ibuprofen. It has been surprisingly discovered that prodrugs of commonly used anti-pyretic, analgesic, or anti-inflammatory drugs can be formulated for systemic delivery using a transdermal drug delivery system. A prodrug refers to an inactive precursor of a drug molecule that is enzymatically or chemically converted in vivo to release the pharmacologically active drug molecule.

The systems of the present invention may comprise one or more prodrugs of one or more anti-pyretic, analgesic, or anti-inflammatory drugs such as but not limited to, acetaminophen, aspirin, celecoxib, diclofenac, diflunisal, etodolac, flurbiprofen, ibuprofen, indomethacin, ketoprofen, ketorolac, meclofenamate, meloxicam, nabumetone, naproxen, nimesulide, oxaprozin, piroxicam, salsalate, sulindac, tolmetin, propoxyphene, codeine, dihydrocodeine, hydrocodone, nalbuphine, meperdine, leverorphanol, hydromorphone, oxymorphone, oxycodone, morphine, methadone, buprenorphine, alfentanil, fentanyl, and sufentanil.

The prodrugs may have improved properties such as improved solubility in lipid membranes, improved stability, improved target selectivity, lower toxicity, etc., relative to the active drug molecule. In some embodiments, the prodrug is selected for increased lipophilicity for improved transport through skin. The prodrug molecule may be an ester, amide, phosphate, carbamate, carbonate, oxime, imine, or an N-Mannich base of an active drug molecule. In some embodiments, a prodrug molecule is obtained by the esterification of a hydroxyl group of the active drug molecule. The active drug molecule may be acylated with an aliphatic or aromatic carboxylic acid. The prodrug molecule may be an acyl, alkyl, aryl, acetyl, carbonate, or carboxylic acid ester of an active drug molecule. The prodrug may also be an amidyl, or a thio-substituted alkyl ester of an active drug molecule.

In one embodiment the prodrug is a compound of formula I:

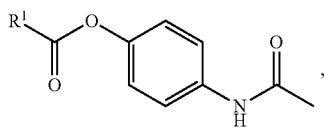

(I)

wherein $R^1$ is selected from optionally substituted $C_1$-$C_6$ alkyl. In one embodiment, $R^1$ is optionally substituted methyl. In one embodiment, $R^1$ is methyl. In one embodiment, $R^1$ is optionally substituted ethyl. In one embodiment, $R^1$ is ethyl. In one embodiment, $R^1$ is optionally substituted propyl. In one embodiment, $R^1$ is optionally substituted n-propyl. In one embodiment, $R^1$ is optionally substituted isopropyl. In one embodiment, $R^1$ is propyl. In one embodiment, $R^1$ is n-propyl. In one embodiment, $R^1$ is isopropyl. In one embodiment, $R^1$ is optionally substituted butyl. In one embodiment, $R^1$ is optionally substituted n-butyl. In one embodiment, $R^1$ is optionally substituted sec-butyl. In one embodiment, $R^1$ is optionally substituted tert-butyl. In one embodiment, $R^1$ is butyl. In one embodiment, $R^1$ is n-butyl. In one embodiment, $R^1$ is sec-butyl. In one embodiment, $R^1$ is tert-butyl.

The present invention relates to transdermal drug delivery systems for the delivery of anti-pyretic, analgesic, or anti-inflammatory drugs and methods of making and using the same. More particularly, the present invention relates to transdermal drug delivery systems for the delivery of prodrugs of commonly used drugs such as acetaminophen and ibuprofen.

In some embodiments, the prodrug is a carboxylate ester of acetaminophen such as, but not limited to, an acetyl, butyrul, hexanoyl, stearoyl, pivalyl, crotonyl, fumaryl, acid succinyl, succinyl, benzoyl, cinnamyl, choroacetyl, or a morpholinoacetyl HCl ester of acetaminophen. In some embodiments, the prodrug is a carbonate ester such as a methyl, ethyl, isopropyl, butyl, isobutyl, hexyl, octyl, chlorethyl, phenyl, or 4-acetaminophenyl ester of acetaminophen.

In another embodiment, the prodrug is an NSAID prodrug (e.g., aspirin, celecoxib, diclofenac, diflunisal, etodolac, flurbiprofen, ibuprofen, indomethacin, ketoprofen, ketorolac, meclofenamate, meloxicam, nabumetone, naproxen, nimesulide, oxaprozin, piroxicam, salsalate, sulindac, and tolmetin). In some embodiments, the NSAID prodrug is an amidyl, a thio, and/or an unsubstituted alkyl ester. In a preferred embodiment, the prodrug is an ibuprofen prodrug. In some embodiments, the prodrug is an ester of ibuprofen such as, but not limited to, methyl, ethyl, n-propyl, iso-propyl, n-butyl, sec-butyl, tert-butyl, n-pentyl, hexyl, heptyl, octyl, lauryl, cetyl, or octadecyl ester.

In one embodiment the prodrug is a compound of formula II:

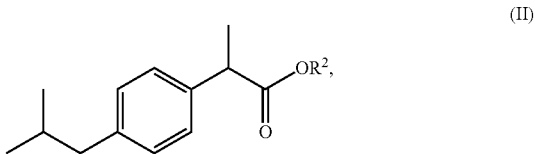

(II)

$R^2$ is selected from optionally substituted $C_1$-$C_6$ alkyl. In one embodiment, $R^2$ is optionally substituted methyl. In one embodiment, $R^2$ is methyl. In one embodiment, $R^2$ is optionally substituted ethyl. In one embodiment, $R^2$ is ethyl. In one embodiment, $R^2$ is optionally substituted propyl. In one embodiment, $R^2$ is optionally substituted n-propyl. In one embodiment, $R^2$ is optionally substituted isopropyl. In one embodiment, $R^2$ is propyl. In one embodiment, $R^2$ is n-propyl. In one embodiment, $R^2$ is isopropyl. In one embodiment, $R^2$ is optionally substituted butyl. In one embodiment, $R^2$ is optionally substituted n-butyl. In one embodiment, $R^2$ is optionally substituted sec-butyl. In one embodiment, $R^2$ is optionally substituted tert-butyl. In one embodiment, $R^2$ is butyl. In one embodiment, $R^2$ is n-butyl. In one embodiment, $R^2$ is sec-butyl. In one embodiment, $R^2$ is tert-butyl.

Suitable salts of a prodrug may include any salt that retains the properties of the prodrug such as effectiveness, solubility, permeability, etc., and may include, for example, hydrochloric, hydrobromic, hydroiodic, phosphoric, sulfuric, nitric, sulfamic, citric, lactic, maleic, pyruvic oxalic, succinic, tartaric, cinnamic, acetic, trifluoroacetic, benzoic, salicylic, gluconic, ascorbic and related pharmaceutically acceptable acid addition salts. In some embodiments, the prodrug is neutral.

A prodrug molecule or a pharmaceutically acceptable salt thereof can be incorporated in the transdermal drug delivery systems of the invention in an effective amount to achieve the desired therapeutic effect. The amount of prodrug or a pharmaceutically acceptable salt thereof, in the transdermal drug delivery systems of the invention may be at any suitable concentration, such as e.g., a therapeutically effective amount. By the phrase "therapeutically effective amount" it is meant any amount of the prodrug that is effective in preventing and/or treating pain, fever, and/or inflammation. The amount of prodrug to be incorporated in the transdermal drug delivery system depends on the particular prodrug, the desired therapeutic effect, and the time span for which the system is intended to provide therapy. In some embodiments, the transdermal drug delivery systems described herein include a therapeutically effective amount of a prodrug.

Generally, the amount of prodrug or a pharmaceutically acceptable salt thereof, is from about 1% to about 50%, from about 1% to about 40%, from about 3% to about 30%, from about 5% to about 40%, from about 1% to about 10%, from about 10% to about 20%, from about 20% to about 30%, from about 30% to about 40%, or from about 40% to about 50% by weight, or a range between and including any two of these values, based on the total dry weight of the polymer matrix or the weight of the liquid or gel reservoir. In specific embodiments, the polymer matrix comprises about 20% to about 30% by weight prodrug based on the total dry weight of the polymer matrix or the weight of the liquid or gel reservoir. In specific embodiments, the polymer matrix comprises about 30% to about 40% by weight prodrug, based on the total dry weight of the polymer matrix or the weight of the liquid or gel reservoir. In specific embodiments, the polymer matrix comprises about 40% to about 50% by weight prodrug based on the total dry weight of the polymer matrix or the weight of the liquid or gel reservoir.

In accordance with any of the embodiments described herein, the transdermal drug delivery system may comprise from about 1 to about 2,500 mg of prodrug or an equivalent amount of a pharmaceutically acceptable salt thereof. In some embodiments, the transdermal delivery system comprises an amount of prodrug selected from the group consisting of about 0.1 to about 5 mg, about 5 to about 10 mg, about 10 to about 15 mg, about 15 to about 20 mg, about 20 to about 25 mg, about 25 to about 30 mg, about 30 to about 35 mg, about 35 to about 40 mg, about 40 to about 45 mg, about 45 to about 50 mg, about 50 to about 55 mg, about 55 to about 60 mg, about 60 to about 65 mg, about 65 to about 70 mg, about 70 to about 75 mg, about 75 to about 80 mg, about 80 to about 85 mg, and a range between and including any two of these values. In some embodiments, the transdermal delivery system comprises an amount of prodrug selected from about 1 to about 50 mg, about 50 to about 100 mg, about 100 to about 150 mg, about 150 to about 200 mg, about 200 to about 300 mg, about 300 to about 350 mg, about 350 to about 450 mg, about 450 to about 500 mg, about 500 to about 1,000 mg, about 1,000 to about 1,500 mg, about 1,500 to about 2,000 mg, about 2,000 to about 2,500 mg, about 2,500 to about 3,000 mg, and a range between and including any two of these values.

In some embodiments, the transdermal delivery system comprises two or more prodrugs, wherein an amount of each prodrug is selected from the group consisting of about 0.1 to about 5 mg, about 5 to about 10 mg, about 10 to about 15 mg, about 15 to about 20 mg, about 20 to about 25 mg, about 25 to about 30 mg, about 30 to about 35 mg, about 35 to about 40 mg, about 40 to about 45 mg, about 45 to about 50 mg, about 50 to about 55 mg, about 55 to about 60 mg, about 60 to about 65 mg, about 65 to about 70 mg, about 70 to about 75 mg, about 75 to about 80 mg, about 80 to about 85 mg, and a range between and including any two of these values. In some embodiments, the transdermal delivery system comprises two or more prodrugs, wherein the amount if each prodrug is each independently selected from the group consisting of about 1 to about 50 mg, about 50 to about 100 mg, about 100 to about 150 mg, about 150 to about 200 mg, about 250 to about 300 mg, about 300 to about 350 mg, about 400 to about 450 mg, about 450 to about 500 mg, about 500 to about 1000 mg, about 1000 to about 1500 mg, about 1500 to about 2000 mg, about 2000 to about 2500 mg, about 2500 to about 3000 mg, and a range between and including any two of these values.

In an exemplary embodiment, the prodrug comprises 4-acetoxyacetanilide. In another exemplary embodiment, the prodrug comprises ethyl 2-(4-isobutylphenyl)-propanoate. In another exemplary embodiment, the prodrug comprises 4-acetoxyacetanilide and ethyl 2-(4-isobutylphenyl)-propanoate.

In an embodiment, the transdermal delivery system comprises 4-acetoxyacetanilide in an amount selected from the group consisting of about 225 to about 275 mg, about 475 to about 525 mg, about 725 to about 775 mg, about 1,225 to about 1,275 mg, and about 2,475 to about 2,525 mg. In an embodiment, the transdermal delivery system comprises 4-acetoxyacetanilide in an amount selected from the group consisting of about 250 mg, about 500 mg, about 750 mg, about 1,250 mg, and about 2,500 mg.

In an embodiment, the transdermal delivery system comprises about 250 mg 4-acetoxyacetanilide and an active surface area of about 2 $cm^2$. In an embodiment, the transdermal delivery system comprises about 500 mg 4-acetoxyacetanilide and an active surface area of about 5 $cm^2$. In an embodiment, the transdermal delivery system comprises about 750 mg 4-acetoxyacetanilide and an active surface area of about 7.5 $cm^2$. In an embodiment, the transdermal delivery system comprises about 1,250 mg 4-acetoxyacetanilide and an active surface area of about 10 $cm^2$. In an embodiment, the transdermal delivery system comprises about 2,500 mg 4-acetoxyacetanilide and an active surface area of about 12.5 $cm^2$.

In an embodiment, the transdermal delivery system comprises ethyl 2-(4-isobutylphenyl)-propanoate in an amount selected from the group consisting of about 225 to about 275 mg, about 350 to about 400 mg, about 600 to about 650 mg, and about 1,225 to about 1,275 mg. In an embodiment, the transdermal delivery system comprises ethyl 2-(4-isobutylphenyl)-propanoate in an amount selected from the group consisting of about 250 mg, about 375 mg, about 625 mg, and about 1,250 mg.

In an embodiment, the transdermal delivery system comprises about 250 mg ethyl 2-(4-isobutylphenyl)-propanoate and an active surface area of about 2 $cm^2$. In an embodiment, the transdermal delivery system comprises about 375 mg ethyl 2-(4-isobutylphenyl)-propanoate and an active surface area of about 3 $cm^2$. In an embodiment, the transdermal delivery system comprises about 625 mg ethyl 2-(4-isobutylphenyl)-propanoate and an active surface area of about 5 $cm^2$. In an embodiment, the transdermal delivery system comprises about 1,250 mg ethyl 2-(4-isobutylphenyl)-propanoate and an active surface area of about 10 $cm^2$.

In some embodiments, the transdermal drug delivery system comprises a concentration of prodrug in the polymer matrix or the liquid or gel reservoir of about 250 to about 500 $mg/cm^3$, about 500 to about 750 $mg/cm^3$, about 750 to about 1,000 $mg/cm^3$, about 1,000 to about 1,250 $mg/cm^3$, and a range between and including any two of these values.

The transdermal drug delivery devices of the invention may additionally comprise additional prodrugs or active agents. In some embodiments, the additional prodrugs or active agents are useful for preventing, treating, reducing or diminishing fever, pain and/or inflammation. Suitable active agents include any active pharmaceutical ingredient known in the art suitable for transdermal delivery and which has shown to mitigate fever, pain, and/or inflammation.

B. Solvents

The transdermal drug delivery systems of the invention can optionally comprise one or more solvents that effectively solubilizes the at least one prodrug. Any suitable solvent can be used in the transdermal drug delivery devices of the invention. The suitability of the solvent may be determined based on the stability of the prodrug in the solvent, the ability of the prodrug to dissolve at high enough concentration levels to allow transdermal delivery of therapeutically effective amounts of the prodrug, etc. In some embodiments, the prodrug molecules may be insoluble or only slightly soluble in water even in an ionized form and dissolution of the prodrug molecules in transdermal formulations may require the incorporation of an alcohol. Exemplary solvents include, but are not limited to, $C_1$-$C_{12}$ alcohols, isopropyl myristate, chloroform, triacetin, N-methyl pyrrolidinone, aliphatic or aromatic alcohols, polyethylene glycols, ethanol, isopropanol, propylene glycol, oleyl alcohol, dimethyl isosorbide, transcutol, and the like; dimethyl sulfoxide (DMSO), dimethyl acetamide, and ethoxydiglycol, and the like. An example of an alcohol useful in the present invention includes, but is not limited to, ethanol. Other short chain alcohols and/or amides may be used. Another alcohol useful in the present invention includes, but is not limited to, polyethylene glycol (e.g., PEG-400).

A combination of two or more solvents may also be used in the transdermal drug delivery devices of the invention. In some embodiments the drug delivery systems of the invention can optionally comprise DMSO and PEG-400. In some embodiments the drug delivery systems of the invention can optionally comprise DMSO and PEG-400 in an about 1:about 1 ratio. In some embodiments the drug delivery systems of the invention can optionally comprise ethanol and PEG-400. In some embodiments the drug delivery systems of the invention can optionally comprise ethanol and PEG-400 in an about 1:about 1 ratio. In some embodiments the drug delivery systems of the invention can optionally comprise ethanol and DMSO. In some embodiments the drug delivery systems of the invention can optionally comprise ethanol and DMSO in an about 2:about 1 ratio. In some embodiments the drug delivery systems of the invention can optionally comprise 10% DMSO in phosphate buffered saline (PBS). In some embodiments, the transdermal drug delivery device of the invention comprises DMSO and about 0.5 mg of sodium metabisulfite. In some embodiments, the transdermal drug delivery device of the invention comprises trimethylamine (TEA). In some embodiments, the transdermal drug delivery device of the invention comprises ethanol. In some embodiments, the transdermal drug delivery device of the invention comprises about 50% PEG 400 (or about 65%, about 60%, about 55%, about 45%, about 40%, or about 35%) in water. In some embodiments, the transdermal drug delivery device of the invention comprises about 50% PEG 400 (or about 65%, about 60%, about 55%, about 45%, about 40%, or about 35%) in ethanol. In some embodiments, the transdermal drug delivery device of the invention comprises about 50% PEG 400 (or about 65%, about 60%, about 55%, about 45%, about 40%, or about 35%) in water comprising about 0.01% TEA.

On a weight to weight percent basis, the transdermal drug delivery devices may include one or more solvents in an amount ranging from about 1.0% to about 40.0%, by weight, of the total weight of the polymer matrix or the weight of the liquid or gel reservoir. In some embodiments, one or more solvents are present in amounts ranging from about 1% to about 40%, about 3% to about 30%, about 5% to about 40%, about 1% to about 10%, about 10% to about 20%, about 20% to about 30%, or about 30% to about 40%, or ranging between and including any two of these values, by weight, of the total weight of polymer matrix or the weight of the liquid or gel reservoir. In some embodiments, the solvent is present in an amount ranging from about 1.0% to about 30.0%, by weight, of the total weight of the polymer matrix or the weight of the liquid or gel reservoir. In other embodiments, the solvent is present in an amount ranging from about 5% to about 15%, by weight, of the total weight of the polymer matrix or the weight of the liquid or gel reservoir. Examples of the amount of solvent as a percentage of the total weight of the polymer matrix or the total weight of the liquid or gel reservoir include about 1.0%, about 2.0%, about 3.0%, about 4.0%, about 5.0%, about 6.0%, about 7.0%, about 8.0%, about 9.0%, about 10.0%, about 12.0%, about 15.0%, about 20.0%, about 25.0%, or about 30.0%, or a range between and including any two of these values.

C. Permeation Enhancers

The transdermal drug delivery systems of the invention can optionally comprise a permeation enhancer. A permeation enhancer is an agent that accelerates the delivery of the prodrug molecule through the skin. A permeation enhancer may refer to agents that improve percutaneous absorption by changing the ability of the stratum corneum to retain moisture, softening the skin, improving the skin's permeability, acting as a permeation assistant, or as a hair-follicle opener, or by changing the state of the skin. Any suitable permeation enhancer may be used in the transdermal drug delivery devices of the invention.

Permeation enhancers may include, but are not limited to, polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are permeation assistants; benzyl nicotinate which is a hair follicle opener; and higher molecular weight aliphatic surfactants such as lauryl sulfate salts which change the surface state of the skin and drugs administered. Other examples of permeation enhancers include, but are not limited to, oleic and linoleic acids, ascorbic acid, panthenol, butylated hydroxytoluene, tocopherol, tocopheryl acetate, tocopheryl linoleate, propyl oleate, and isopropyl palmitate, dimethyl sulfoxide (DMSO), polyethylene glycol monolaurate, alkyl lactams, long chain amides, and substituted 1,3-dioxacyclopentanes and substituted 1,3-dioxacyclohexanes. Surfactants such as Tween 80, labrasol, and cremophor and nonionic surfactants such as polyoxyethylene behenyl ether, polyoxyethylene hexyl decyl ether, and polyoxyethylene decyl tetradecyl ether may also be used as a permeation enhancer.

In some embodiments, the permeation enhancer is a glycol such as polyethylene glycol. In some embodiments, the permeation enhancer comprises polyethylene glycols having a molecular weight of up to 1,000 (e.g., PEG-200, PEG-300, PEG-400, PEG-600, or mixtures thereof). In some embodiments, the permeation enhancer is PEG-200, PEG-300, PEG-400, PEG-600, PEG-[950-1,050], PEG-1,000, PEG-[1,300-1,600], PEG-[1,305-1,595], PEG-1,450, PEG-1,500, PEG-2,000, PEG-2,050, PEG-3,000, PEG-[3,000-3,700], PEG-3,350, PEG-4,000, PEG-4,600, PEG-6,000, PEG-8,000, PEG-10,000, PEG-12,000, PEG-20,000, or PEG-35,000, or any combination thereof. In specific embodiments, the polyethylene glycol is PEG-400. In some embodiments, the permeation enhancer is another glycol, such as dipropylene glycol, propylene glycol, or butylene glycol. In some embodiments, the permeation enhancer is oleyl alcohol. In some embodiments, the penetration enhancer is DMSO. In other embodiments, the penetration enhancer comprises a mixture of at least two permeation enhancers. For example, a permeation enhancer may comprise DMSO and one or more polyhydric alcohols, such as polytheylene glycol, dipropylene glycol, propylene glycol, or butylene glycol. For instance, the permeation enhancer may comprise a combination of DMSO and polyethylene glycol (e.g., PEG-400).

In some embodiments, a permeation enhancer is used in an amount up to about 30% by weight, of the total weight of the polymer matrix or the weight of the liquid or gel reservoir, including up to 30% by weight, up to about 20% by weight, including 20% by weight, or up to about 10% by weight, up to 10% by weight, or up to 5% by weight, including up to 5% by weight, of the total weight of the polymer matrix or the weight of the liquid or gel reservoir. In some embodiments, a penetration enhancer is used in an amount of from about 5% to about 15%, such as from 5% to 15%, by weight, of the total weight of the polymer matrix or the weight of the liquid or gel reservoir. In specific embodiments, the permeation enhancer comprises a mixture of DMSO and polyethylene glycol. In some embodiments, the permeation enhancer comprises a mixture of DMSO and polyethylene glycol-400, in a mass ratio of about 1:about 1. In some embodiments the permeation enhancer comprises ethanol and PEG-400. In some embodiments the permeation enhancer comprises ethanol and PEG-400 in an about 1:about 1 ratio. In some embodiments the permeation enhancer comprises ethanol and DMSO. In some embodiments the permeation enhancer comprises ethanol and DMSO in an about 2:about 1 ratio.

D. Additional Ingredients

The transdermal drug delivery systems of the invention can optionally further comprise various thickeners, fillers, and other additives or components known for use in transdermal drug delivery systems. Other additives may include a tackifier, a plasticizer, or an anti-oxidant. The additional components may be present in the prodrug-comprising layer, or some other layer of the transdermal drug delivery system. The transdermal drug delivery systems of the invention can additionally and optionally include additives such as, but not limited to, humectants, bulking agents, viscosity promoting agents, coloring agents, pharmaceutically acceptable excipients, microbial preservatives, perfume, pH adjusters, buffers, etc. as long as they do not diminish the efficacy of the prodrug.

Thickening or gelling agents suitable may be used to increase the viscosity of the prodrug composition. Examples of thickening or gelling agents that may be used in the transdermal drug delivery systems of the invention include, but are not limited to, neutralized anionic polymers or neutralized carbomers, such as polyacrylic acid (CARBOPOL™ by Noveon, Inc., Cleveland, Ohio), carboxypolymethylene, carboxymethylcellulose and the like, including derivatives of Carbopol™ polymers, such as Carbopol™ Ultrez 10, Carbopol™ 940, Carbopol™ 941, Carbopol™ 954, Carbopol™ 980, Carbopol™ 981, Carbopol™ ETD 2001, Carbopol™ EZ-2 and Carbopol™ EZ-3. Also suitable are other known polymeric thickening agents, such as Pemulen™ polymeric emulsifiers, Noveon™ polycarbophils, and Klucel™. Additional thickening agents, enhancers and adjuvants may generally be found in Remington's The Science and Practice of Pharmacy as well as the Handbook of Pharmaceutical Excipients, Arthur H. Kibbe ed. 2000. Thickening agents or gelling agents are present in an amount sufficient to provide the desired rheological properties of the composition.

Humectants may include dexpanthenol, glycerin, glycerol, aloe vera, etc. Microbial preservatives may include, but are not limited to, methylparaffin, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof.

The transdermal drug delivery systems of the invention may optionally include at least one pH adjuster. Suitable pH adjusters include, but are not limited to, diethyanolamine, lactic acid, citric acid, hydrochloric acid, monoethanolamine, triethylanolamine, sodium hydroxide, sodium phosphate, semi-synthetic derivatives thereof, and combinations thereof. The transdermal drug delivery systems of the invention may further optionally include a buffering agent, such as a pharmaceutically acceptable buffering agent.

In addition to the foregoing additives, the transdermal drug delivery systems of the invention may also comprise inert and physiologically acceptable carriers or diluents. These additives, if present, can be incorporated in the transdermal drug delivery systems at a concentration in the range of about 0.001%, about 0.01%, about 0.02%, about 0.05%, about 0.1%, about 0.5%, about 1%, about 2%, about 5%, about 10%, about 15%, about 20%, about 30%, about 40%, about 50%, about 60%, about 70%, and ranges between any two of these values or less than any one of these values, by weight, of the total weight of the polymer matrix or the weight of the liquid or gel reservoir.

III. Stability

The transdermal drug delivery systems are stable for an extended period of time. In some embodiments, the transdermal drug delivery systems have a shelf life of one year or more. In some embodiments, the transdermal drug delivery systems have a shelf life of two years or more.

In one aspect, the present invention provides transdermal drug delivery systems which are thermostable. For example, the transdermal drug delivery systems of the invention can be stable when exposed to room temperature (e.g., about 25° C.) and up to about 50° C. In other embodiments, the transdermal drug delivery systems of the invention are stable when exposed to a temperature selected from the group consisting of greater than about 30° C., greater than about 35° C., greater than about 40° C., greater than about 45° C., greater than about 50° C., about 55° C. or greater than about 55° C., about °60 C or greater than about 60° C., about 65° C. or greater than about 65° C., about 70° C. or greater than about 70° C., about 75° C. or greater than about 75° C., about 80° C. or greater than about 80° C., or about 85° C. or greater than about 85° C.

In addition, the transdermal drug delivery systems of the invention can be stable when exposed to an elevated temperature for a duration of about 1 month to about 3 years. In some embodiments, the transdermal drug delivery systems of the invention can be stable when exposed to an elevated temperature of about 25° C., about 30° C., about 35° C. about 40° C., about 45° C. or about 50° C. for a duration of about 3 months to about 2 years. In some embodiments, the transdermal drug delivery systems of the invention can be stable when exposed to room temperature storage for a duration of about 3 months to about 2 years. In some embodiments, the transdermal drug delivery systems of the invention can be stable when exposed to room temperature storage for up to about 2 years.

IV. Methods of Making the Transdermal Drug Delivery Systems

The transdermal drug delivery systems described herein can be prepared by methods known in the art. For instance, for a matrix system transdermal drug delivery system, the polymer matrix can be prepared by methods known in the art, such as blending (mixing) the components of the polymer matrix in powder or liquid form with an appropriate amount of drug in the presence of an appropriate solvent, such as a volatile organic solvent, optionally with other excipients. To form a final product, the drug/polymer/solvent mixture may be cast onto a support layer such as the backing layer or release liner (optionally, at ambient temperature and pressure) followed by evaporation of the volatile solvent(s), for example, at room temperature, slightly elevated temperature, or by a heating/drying step, to form the drug-containing polymer matrix on a backing layer or release liner. Additional support layers may be added and systems of appropriate shape and size may be die-cut. The order of steps, amount of ingredients, and the amount of time of blending or mixing can be determined and optimized by one of skill in the art.

In accordance with any of the embodiments of the transdermal drug delivery systems described herein, in some embodiments, the coat weight of the polymer matrix can be, from about 50 mg/cm$^2$ to about 300 mg/cm$^2$, based on the active surface area of the polymer matrix. In some embodiments, the coat weight of the polymer matrix can be, from about 50 to about 75 mg/cm$^2$, about 75 to about 100 mg/cm$^2$, about 100 to about 125 mg/cm$^2$, about 125 to about 150 mg/cm$^2$, about 150 to about 175 mg/cm$^2$, about 175 to about 200 mg/cm$^2$, about 200 to about 225 mg/cm$^2$, about 225 to about 250 mg/cm$^2$, about 250 to about 300 mg/cm$^2$, and a range between and including any two of these values, based on the active surface area of the polymer matrix.

In accordance with any of the embodiments of the transdermal drug delivery systems described herein, in some embodiments, the prodrug may be present, in an amount from about 50 mg/cm$^2$ to about 300 mg/cm$^2$, based on the active surface area of the of the polymer matrix or liquid or gel reservoir. In some embodiments, the prodrug may be present, in an amount from about 50 to about 75 mg/cm$^2$, about 75 to about 100 mg/cm$^2$, about 100 to about 125 mg/cm$^2$, about 125 to about 150 mg/cm$^2$, about 150 to about 175 mg/cm$^2$, about 175 to about 200 mg/cm$^2$, about 200 to about 225 mg/cm$^2$, about 225 to about 250 mg/cm$^2$, about 250 to about 300 mg/cm$^2$, and a range between and including any two of these values, based on the active surface area of the of the polymer matrix. Exemplary amounts include about 75 mg/cm$^2$, about 100 mg/cm$^2$, and about 150 mg/cm$^2$.

In accordance with any of the embodiments of the transdermal drug delivery systems described herein, in some embodiments, the system (e.g. a transdermal patch) has a skin contact region having an area from about 1 to about 50 cm$^2$. Exemplary embodiments include a skin contact region having an area from about 0.5 to about 5 cm$^2$, about 5 to about 10 cm$^2$, about 10 to about 15 cm$^2$, about 15 to about 20 cm$^2$, about 20 to about 25 cm$^2$, about 25 to about 30 cm$^2$, about 30 to about 35 cm$^2$, about 35 to about 40 cm$^2$, about 40 to about 45 cm$^2$, or about 45 to about 50 cm$^2$. In some embodiments, the system has a skin contact region of about 2.5 cm$^2$, about 3 cm$^2$, about 5 cm$^2$, about 7.5 cm$^2$, about 10 cm$^2$, about 12.5 cm$^2$, about 25 cm$^2$, about 30 cm$^2$, about 40 cm$^2$, or about 50 cm$^2$.

In accordance with any of the embodiments of the transdermal drug delivery systems described herein, in some embodiments, the system (e.g. a transdermal patch) has an active surface area having an area from about 1 to about 200 cm$^2$. Exemplary embodiments include an active surface area having an area from about 5 to about 150 cm$^2$, about 10 to about 150 cm$^2$, about 10 to about 100 cm$^2$, about 10 to about 50 cm$^2$, about 5 to about 50 cm$^2$, about 5 to about 25 cm$^2$, about 2 to about 25 cm$^2$, about 2 to about 15 cm$^2$, or about 2 to about 10 cm$^2$. In some embodiments, the system has an active surface area about 2.5 cm$^2$, about 3 cm$^2$, about 5 cm$^2$, about 7.5 cm$^2$, about 10 cm$^2$, about 12.5 cm$^2$, about 15 cm$^2$, about 20 cm$^2$, about 25 cm$^2$, about 30 cm$^2$, about 40 cm$^2$, or about 50 cm$^2$.

The amount of prodrug to be incorporated in the polymer matrix or liquid or gel reservoir varies depending on the particular drug, the desired therapeutic effect, and the time span for which the system is to provide therapy. For most prodrugs, the passage of the drugs through the skin will be the rate-limiting step in delivery. A minimum amount of prodrug in the system is selected based on the amount of prodrug which passes through the skin in the time span for which the system is to provide therapy. In some embodiments, a system for the transdermal delivery of a prodrug is used over a period of about 4 hours, about 8 hours, about 12 hours, about 18 hours, about 1 day, about 2 days, about 3 days, or longer. Thus, in some embodiments, the systems comprise an amount of prodrug (e.g., an acetaminophen prodrug or an NSAID prodrug) sufficient to deliver therapeutically effective amounts of drug (upon conversion to the active form of the drug) over a period of from about 4 hours, about 8 hours, about 12 hours, about 18 hours, about 1 day, about 2 days, about 3 days, or longer. In some embodiments, a therapeutically effective amount of prodrug is from about 100-500 mg/day, 500-1,000 mg/day, 1,000-1,500 mg/day, 1,500-2,000 mg/day, 2,000-3,000 mg/day, or a range between and including any two of these values. As noted above, in some embodiments, these rates are achieved over a duration of application of at least about 4 hours, about 8 hours, about 12 hours, about 18 hours, or about 1 day. In some embodiments, the prodrug is an acetaminophen prodrug and therapeutically effective amounts of the acetaminophen prodrug may be calculated based on a therapeutically effective plasma concentration of acetaminophen in the range of about 5 to about 20 μg/ml. In some embodiments, the prodrug is an ibuprofen prodrug and therapeutically effective amounts of the ibuprofen prodrug may be calculated based on a therapeutically effective plasma concentration of ibuprofen in the range of about 5 to about 25 μg/ml.

VI. Methods of Using the Transdermal Delivery Systems of the Invention

One aspect of the invention provides methods of treating, preventing, minimizing, and/or diminishing pain, fever, and/or inflammation, using a transdermal drug delivery system of the invention. The transdermal drug delivery systems of the invention comprise safe and effective amounts of an anti-pyretic, analgesic, or anti-inflammatory prodrug and can be applied to the skin or mucosa of a subject in need thereof to treat, prevent, minimize, and/or diminish pain, fever, and/or inflammation.

The transdermal drug delivery systems may comprise such amounts or submultiples thereof of the prodrug as may be used to make up the daily dose of the active form of the drug. It will be understood, however, that the specific dose level for any particular subject will depend upon a variety of factors: the type and degree of response to be achieved; activity of the specific agent or composition employed; the specific agents or composition employed; the age, body weight, general health, sex, and diet of the subject; the duration of the treatment; drugs used in combination or coincidental with the specific agent; and like factors well known in the medical arts.

The methods of the invention also includes treatment of any condition which can be treated with an antipyretic, analgesic, or anti-inflammatory drug. For example, a transdermal patch comprising an acetaminophen prodrug may be used to treat any condition which can be treated with acetaminophen or a transdermal patch comprising an ibuprofen prodrug may be used to treat any condition which can be treated with ibuprofen. An exemplary acetaminophen prodrug is 4-acetoxyacetanilide. An exemplary ibuprofen prodrug is ethyl 2-(4-isobutylphenyl)-propanoate.

In some embodiments, the methods of the invention include treating, preventing, minimizing, and/or diminishing fever in a subject in need by applying a transdermal drug delivery system of the invention to the skin of or mucosa of the subject. The transdermal delivery systems of the invention may comprise a suitable prodrug of an anti-pyretic drug (e.g., acetaminophen and/or an NSAID such as ibuprofen). In a specific embodiment, a method of the invention comprises treating, preventing, minimizing and/or diminishing fever in a subject in need by applying a transdermal patch comprising an acetaminophen prodrug to the skin or mucosa of the subject. An exemplary acetaminophen prodrug is 4-acetoxyacetanilide. In another specific embodiment, a method of the invention comprises treating, preventing, minimizing and/or diminishing fever in a subject in need by applying a transdermal patch comprising an ibuprofen prodrug to the skin or mucosa of the subject. An exemplary ibuprofen prodrug is ethyl 2-(4-isobutylphenyl)-propanoate.

In some embodiments, the methods of the invention include treating, preventing, minimizing, and/or diminishing pain in a subject in need by applying a transdermal drug delivery system of the invention to the skin or mucosa of the subject. The transdermal delivery systems of the invention may comprise a suitable prodrug of an analgesic drug (e.g., acetaminophen and/or an NSAID such as ibuprofen). In a specific embodiment, a method of the invention comprises treating, preventing, minimizing and/or diminishing pain in a subject in need by applying a transdermal patch comprising an acetaminophen prodrug to the skin or mucosa of the subject. An exemplary acetaminophen prodrug is 4-acetoxyacetanilide. In another specific embodiment, a method of the invention comprises treating, preventing, minimizing and/or diminishing fever in a subject in need by applying a transdermal patch comprising an ibuprofen prodrug to the skin or mucosa of a subject. An exemplary ibuprofen prodrug is ethyl 2-(4-isobutylphenyl)-propanoate. The pain may be musculoskeletal pain, neuropathic pain, nociceptive pain, inflammatory pain, headache, connective tissue pain, arthritic pain (e.g., pain associated with rheumatoid arthritis or juvenile rheumatoid arthritis), chronic pain, acute pain, or pain associated with injury or any pain or discomfort that is commonly treated with an analgesic drug.

In yet other embodiments, the methods of the invention include treating, preventing, minimizing, and/or diminishing inflammation in a subject in need, the method comprising applying a transdermal drug delivery system of the invention to the skin or mucosa of the subject. In some embodiments, a method of the invention comprises treating, preventing, minimizing and/or diminishing fever in a subject in need, the method comprising applying a transdermal patch comprising a prodrug of an NSAID to the skin or mucosa of the subject. In a specific embodiment, a method of the invention comprises treating, preventing, minimizing, and/or diminishing inflammation in a subject in need by applying a transdermal patch comprising an ibuprofen prodrug to the skin or mucosa of a subject. An exemplary ibuprofen prodrug is ethyl 2-(4-isobutylphenyl)-propanoate.

In some embodiments, the transdermal drug delivery systems are designed for use in uncooperative patient populations, for example, pediatric or geriatric patients. The prodrug delivery rate, total duration of prodrug release, the active surface area, etc. of the delivery system (e.g., a transdermal patch) may be adjusted for use in different patient populations (e.g., neonates, infants, toddler, children, adolescents, adults, and geriatric) based upon the dosage guidelines for each patient sub-group. In some embodiments, the subject is a neonate. In some embodiments, the subject is a newborn or infant up to 1 year of age. In some embodiments, the subject is a child between the age of 1-3 years. In some embodiments, the subject is a child between the age of 1-6 years. In some embodiments, the subject is a child between the age of 6-12 years. In some embodiments, the subject is a child between the age of 12-18 years. In some embodiments, the subject is an adult between the ages of 18-65 years. In some embodiments, the subject is an adult greater than 65 years of age. In some embodiments, the subject is unable to or unwilling to take an oral dose of the active form of an anti-pyretic, analgesic, or anti-inflammatory drug (e.g. acetaminophen or a commonly used NSAID such as ibuprofen). In some embodiments, the subject has vomiting or diarrhea. In some embodiments, the subject has trouble swallowing. In some embodiments, the subject is unable to take a full oral dose of an anti-pyretic, analgesic, or anti-inflammatory drug (e.g., acetaminophen or a commonly used NSAID such as ibuprofen) for any reason.

In exemplary embodiments, (1) the subject weighs between about 6 and about 11 lbs, and the transdermal delivery system comprises about 200 to 300 mg, such as about 250 mg, 4-acetoxyacetanilide, and an active surface area of about 1 to about 3 $cm^2$, such as about 2 $cm^2$; (2) the subject weighs between about 12 and about 17 lbs. and the transdermal delivery system comprises about 400 to about 600 mg, such as about 500 mg, 4-acetoxyacetanilide, and an active surface area of about 4 to about 6 $cm^2$, such as about 5 $cm^2$; (3) the subject weighs between about 8 and about 23 lbs. and the transdermal delivery system comprises about 550 to about 850 mg, such as about 750 mg, 4-acetoxyacetanilide, and an active surface area of about 5 to about 9 $cm^2$, such as about 7.5 $cm^2$; (4) the subject weighs between about 24 and about 47 lbs. and the transdermal delivery system comprises about 1000 to about 1500 mg, such as about 1,250 mg, 4-acetoxyacetanilide, and an active surface area of about 8 to about 12 $cm^2$, such as about 10 $cm^2$; or (5) the subject weighs between about 48 and about 95 lbs. and the transdermal delivery system comprises about 2000 to about 3000 mg, such as about 2,500 mg, 4-acetoxyacetanilide, and an active surface area of about 10 to about 15 $cm^2$, such as about 12.5 $cm^2$.

In exemplary embodiments, (1) the subject weighs between about 12 and about 17 lbs. and the transdermal delivery system comprises about 200 to 300 mg, such as about 250 mg, ethyl 2-(4-isobutylphenyl)-propanoate and an active surface area of about 1 to about 3 $cm^2$, such as about 2 $cm^2$; (2) the subject weighs between about 8 and about 23 lbs. and the transdermal delivery system comprises about 275 to about 475 mg, such as about 375 mg, ethyl 2-(4-isobutylphenyl)-propanoate and an active surface area of about 1 to about 5 $cm^2$, such as about 3 $cm^2$; (4) the subject weighs between about 24 and about 47 lbs. and the transdermal delivery system comprises about 525 to about 725 mg, such as about 625 mg, ethyl 2-(4-isobutylphenyl)-propanoate and an active surface area of about 4 to about 6 $cm^2$, such as about 5 $cm^2$; (5) the subject weighs between about 48 and about 95 lbs. and the transdermal delivery system comprises about 1000 to about 1500 mg, such as about 1,250 mg, ethyl 2-(4-isobutylphenyl)-propanoate, and an active surface area of about 8 to about 12 cm$^2$, such as about 10 cm$^2$.

The transdermal drug delivery systems of the invention may be applied to any suitable site on the subject's body. Suitable sites for topical application of a system of the invention include, but are not limited to, the chest (e.g., upper chest or lower chest), upper arm, hip, back (e.g., upper back, mid-section of the back, lower back), abdomen (e.g., upper abdomen, mid-section of the abdomen, lower abdomen), buttock, upper torso, lower torso, flank, shoulder, or thigh (e.g., upper thigh, inner thigh, or lower thigh). Depending on the prodrug, it is possible that particular sites may be contraindicated for transdermal delivery.

One of the advantages of a transdermal drug delivery system is that treatment can be quickly interrupted or stopped by removing the system. However, typically, the systems of the invention may be designed to deliver a therapeutically effective amount of the prodrug (upon conversion to the active form of the drug) over a period of time of about 4 to about 24 hours, or any time point in-between these two values. In some embodiments, a transdermal drug delivery system of the invention delivers a therapeutically effective amount of the prodrug over a period of time of about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours, or ranging between and including any two of the values above. In another embodiment, a transdermal drug delivery system of the invention delivers a therapeutically effective amount of the prodrug over a period of time of about 26 hours, about 28 hours, about 30 hours, about 32 hours, about 34 hours, about 36 hours, about 38 hours, about 40 hours, about 42 hours, about 44 hours, about 46 hours, about 48 hours, about 50 hours, about 52 hours, about 54 hours, about 56 hours, about 58 hours, about 60 hours, about 62 hours, about 64 hours, or about 66 hours, or about 68 hours, or about 70 hours, or about 72 hours, or ranging between and including any two of the values above.

In some embodiments, the analgesic prodrug has a lag time between about 2 to about 2.5 hours. In some embodiments, the analgesic prodrug has a lag time between about 2.5 to about 3 hours. In some embodiments, the analgesic prodrug has a lag time between about 3 to about 3.5 hours. In some embodiments, the analgesic prodrug has a lag time between about 3.5 to about 4 hours. In some embodiments, the analgesic prodrug has a lag time between about 4 to about 4.5 hours. In some embodiments, the analgesic prodrug has a lag time between about 4.5 to about 5 hours. In some embodiments, the analgesic prodrug has a lag time between about 5 to about 5.6 hours. In some embodiments, the analgesic prodrug has a lag time between about 5.5 to about 6 hours.

In some embodiments, the analgesic prodrug has a permeability coefficient between about 2 to about 2.5 µg/h/cm$^2$. In some embodiments, the analgesic prodrug has a permeability coefficient between about 2.5 to about 3 µg/h/cm$^2$. In some embodiments, the analgesic prodrug has a permeability coefficient between about 3 to about 3.5 µg/h/cm$^2$. In some embodiments, the analgesic prodrug has a permeability coefficient between about 3.5 to about 4 µg/h/cm$^2$. In some embodiments, the analgesic prodrug has a permeability coefficient between about 4 to about 4.5 µg/h/cm$^2$. In some embodiments, the analgesic prodrug has a permeability coefficient between about 4.5 to about 5 µg/h/cm$^2$. In some embodiments, the analgesic prodrug has a permeability coefficient between about 5 to about 5.6 µg/h/cm$^2$. In some embodiments, the analgesic prodrug has a permeability coefficient between about 5.5 to about 6 µg/h/cm$^2$.

II. Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not exclude others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The phrase "substantially free" as used herein means that the described composition comprises less than about 5%, less than about 3%, or less than about 1% by weight, based on the total weight of the composition at issue, of the excluded component(s).

The phrase "free of" as used herein means that the described composition (e.g., polymer matrix, etc.) is formulated without adding the excluded component(s) as an intended component, although trace amounts may be present in other components or as a by-product or contaminant, such that the composition comprises at most only trace amounts of the excluded component(s). In some embodiments, the compositions and systems described herein are formulated without any other systemically active drug other than norethindrone acetate.

As used herein "subject" refers to organisms to be treated by the compositions of the present invention. Such organisms include animals (domesticated animal species, wild animals), preferably a mammal, including a human or non-human. The terms patient and subject may be used interchangeably.

As used herein, the terms the terms "transdermal" and "transdermally" refer to passage through the skin or mucosa (including oral, buccal, nasal, rectal and vaginal mucosa), into systemic circulation. Thus, the delivery systems described herein may be applied topically to a subject to achieve transdermal delivery of a drug or prodrug.

As used herein, "transdermal drug delivery system" refers to a system (e.g., a device) comprising a composition that releases drug upon application to the skin (or any other surface noted above). A transdermal drug delivery system may comprise a drug-containing layer, and, optionally, a backing layer and/or a release liner layer. In some embodiments, the transdermal drug delivery system is a substantially non-aqueous, solid form, capable of conforming to and adhering to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in some embodiments, a transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin. In some embodiments, the transdermal drug delivery system comprises a skin-contacting face adhesive layer. Additionally or alternatively, the system may comprise a rate-controlling membrane.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with drug dissolved or dispersed therein. The polymer matrix also may comprise tackifiers, plasticizers, crosslinking agents, enhancers, co-solvents, fillers, antioxidants, solubilizers, crystallization inhibitors, or other additives described herein.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

In some embodiments, the polymer matrix is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix has a glass transition temperature (Tg), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers to which they are added.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. Exemplary therapeutically effective amounts and therapeutic levels are provided below. Those skilled in the art can adjust such amounts in accordance with standard practices as needed to treat a specific subject and/or condition/disease.

As used herein, "active surface area" means the surface area of the drug-containing polymer matrix of the transdermal drug delivery system.

As used herein, "coat weight" refers to the weight of the drug-containing layer per unit area of the active surface area of the transdermal drug delivery system.

As used herein, "flux" (also called "permeation rate") is defined as the absorption of a drug through skin or mucosal tissue, and is described by Fick's first law of diffusion:

$$J = -D \, (dCm/dx)$$

where J is the flux in $g/cm^2/hr$, D is the diffusion coefficient of the drug through the skin or mucosa in $cm^2/hr$ and dCm/dx is the concentration gradient of the drug across the skin or mucosa.

As used herein, "permeability coefficient" refers to the mass or volume flowing through the skin per unit area per unit time.

As used herein "lag time" refers to a delay of time between drug administration and the beginning of drug absorption.

"Carriers" or "vehicles" as used herein refer to carrier materials suitable for incorporation in a transdermal delivery system (e.g. transdermal patch). Carriers and vehicles useful herein include any such materials known in the art, which are nontoxic and do not interact with other components of the formulation in which it is contained in a deleterious manner.

The terms "pharmaceutically acceptable" or "pharmacologically acceptable," as used herein, refer to compositions that do not substantially produce adverse allergic or immunological reactions when administered to a host (e.g., an animal or a human). As used herein, "pharmaceutically acceptable carrier" includes any and all solvents, dispersion media, coatings, wetting agents, isotonic and absorption delaying agents, disintegrants, and the like.

The terms "treat," "treating" and "treatment" as used herein refer to reduction in severity and/or elimination of pain, fever, and/or inflammation.

An "effective amount" is an amount sufficient to effect beneficial or desired results. An effective amount can be administered in one or more administrations, applications or dosages and is determined by the system in which the drug or compound is delivered, e.g., an effective amount for in vitro purposes is not the same as an effective amount for in vivo purposes. For in vivo purposes, the delivery and "effective amount" is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Optionally substituted" refers to a group selected from that group and a substituted form of that group. A "substituted" group, refers to that group substituted with any substituent described or defined below. Substituted groups are defined herein. For example, an optionally substituted alkyl, intends and alkyl group optionally substituted [a C—H bond is replaced with] one or more $C_1$-$C_{12}$ alkyl, $C_1$-$C_{12}$ alkenyl, $C_1$-$C_{12}$ alkynyl, $C_1$-$C_{12}$ alkoxy, $C_1$-$C_{12}$ cycloalkyl, acyl, acylamino, acyloxy, amino, aminocarbonyl, or any of the chemical groups defined.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n propyl ($CH_3CH_2CH_2$—), isopropyl (($CH_3)_2CH$—), n butyl ($CH_3CH_2CH_2CH_2$—), isobutyl (($CH_3)_2CHCH_2$—), sec butyl (($CH_3$)($CH_3CH_2$)CH—), t butyl (($CH_3)_3C$—), n pentyl ($CH_3CH_2CH_2CH_2CH_2$—), and neopentyl (($CH_3)_3CCH_2$—). A Cx-Cy alkyl will be understood to have from x to y carbons.

"Alkenyl" refers to monovalent straight or branched hydrocarbyl groups having from 2 to 6 carbon atoms and preferably 2 to 4 carbon atoms and having at least 1 and preferably from 1 to 2 sites of vinyl ($>C=C<$) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (C≡C) unsaturation. Examples of such alkynyl groups include acetylenyl (C≡CH), and propargyl (—$CH_2$CCH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups preferably having from 1 to 6 and more preferably 1 to 3 carbon atoms that are either straight chained or branched. This term is exemplified by groups such as methylene (—$CH_2$—), ethylene ($CH_2CH_2$—), n propylene (—$CH_2CH_2CH_2$—), iso propylene (—$CH_2CH$ ($CH_3$)— or —$CH(CH_3)CH_2$—), butylene (—$CH_2CH_2CH_2CH_2$—), isobutylene (—$CH_2CH(CH_3)$ $CH_2$—), sec butylene (—$CH_2CH_2(CH_3)CH$—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —$NR^Q$— moieties where $R^Q$ is H or $C_1$-$C_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}C(O)$alkyl, —$NR^{47}C(O)$substituted alkyl, —$NR^{47}C(O)$cycloalkyl, —$NR^{47}C(O)$substituted cycloalkyl, —$NR^{47}C(O)$cycloalkenyl, —$NR^{47}C(O)$substituted cycloalkenyl, —$NR^{47}C(O)$alkenyl, —$NR^{47}C(O)$substituted alkenyl, —$NR^{47}C(O)$alkynyl, —$NR^{47}C(O)$substituted alkynyl, —$NR^{47}C(O)$aryl, —$NR^{47}C(O)$substituted aryl, —$NR^{47}C(O)$heteroaryl, —$NR^{47}C(O)$substituted heteroaryl, —$NR^{47}C(O)$heterocyclic, and —$NR^{47}C(O)$substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl —C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group $NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —$C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H 1,4 benzoxazin 3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azide" refers to the group —N=N

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{47}$C(O)O-alkyl, —NR$^{47}$C(O)O-substituted alkyl, —NR$^{47}$C(O)O-alkenyl, —NR$^{47}$C(O)O-substituted alkenyl, —NR$^{47}$C(O)O-alkynyl, —NR$^{47}$C(O)O-substituted alkynyl, —NR$^{47}$C(O)O-aryl, —NR$^{47}$C(O)O-substituted aryl, —NR$^{47}$C(O)O-cycloalkyl, —NR$^{47}$C(O)O-substituted cycloalkyl, —NR$^{47}$C(O)O-cycloalkenyl, —NR$^{47}$C(O)O-substituted cycloalkenyl, —NR$^{47}$C(O)O-heteroaryl, —NR$^{47}$C(O)O-substituted heteroaryl, —NR$^{47}$C(O)O-heterocyclic, and —NR$^{47}$C(O)O-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one $R^{53}$ is not hydrogen, and wherein said substituents are as defined herein.

"Halo" or "halogen" refers to fluoro, chloro, bromo and iodo.

"Hydroxy" or "hydroxyl" refers to the group —OH or protected forms thereof, e.g. —$OP^z$.

A "protecting group" or "$P^z$" (wherein z is an integer) intends any protecting group for an alcohol(s) well known in the art. Non-limiting examples include 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TB S, TBDMS), or tert-butyldiphenylsilyl ether (TBDPS). In the case of a 1,2 diol suitable protecting groups include acetonide, benzaldehyde acetal or carbonate. These protecting groups and others are well known to the skilled artisan, as evidenced by Green et al: Greene's Protective Groups in Organic Synthesis, Fourth Edition Author(s): Peter G. M. Wuts and Theodora W. Greene First published: 10 Apr. 2006, Copyright © 2007 John Wiley & Sons, Inc, the disclosure of which is incorporated by reference.

"Deprotection," "deprotecting," and the like, intend removal of the protecting group by any conventional means known to the skilled artisan or present in Green et al. It will be readily apparent that the conditions for deprotecting depend upon which protecting group is used.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —$NO_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

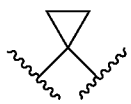 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, -phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

VII. Examples

The invention is further described by reference to the following examples, which are provided for illustration only. The invention is not limited to the examples, but rather includes all variations that are evident from the teachings provided herein. All publicly available documents referenced herein, including but not limited to U.S. patents and U.S. patent publications, are specifically incorporated by reference.

Example 1

The purpose of this example was to evaluate the stability, solubility, and skin permeation characteristics of an exemplary acetaminophen prodrug (Pro-APAP), 4-acetoxyacetanilide, to determine its potential for transdermal delivery. 4-acetoxyacetanilide (CAS Number: 2623-33-8) has a molecular weight of 193.20 g/mol and a melting point of 151-155° C., and is slightly soluble in chloroform, DMSO, and methanol.

4-acetoxyacetanilide was assessed for its ability to be soluble in high concentrations in a model solvent/vehicle that can be used in a transdermal device/patch system and achieve therapeutic drug dosage levels. The ability of the compound to remain stable in the solvent/vehicle was also tested and evaluated.

First, a suitable assay for detecting 4-acetoxyacetanilide was developed. FIG. 1 shows the calibration of an ultraviolet/visible (UV-Vis) spectrometer (Tecan m200 Infinity Multi-Well Plate Reader) for use in determining the concentration of 4-acetoxyacetanilide by detecting absorbance at 246 nm. Ethanol was used as the calibration standard diluent. Second, after screening several blends and co-solvents, a formulation of 50% DMSO in Polyethylene Glycol 400 was selected as the model solvent/vehicle for further testing. The Pro-APAP compound, 4-acetoxyacetanilide, was visually screened for physical and chemical stability over a 4-week period.

Skin Permeation Studies: Upon completion of the solubility and stability studies, the ability of the compound to permeate the skin in the selected solvent/vehicle was tested and the rate of permeation was measured to determine whether the compound permeated to an extent relevant for clinical use in a transdermal patch. Specifically, 4-acetoxyacetanilide was assessed for skin permeation across human skin over a 24 h time period.

Methods: For the skin permeation studies, a sample chamber containing 5 mL of 50% Polyethylene glycol 400 in ethanol was used as the receptor media. An initial sample of receptor media was drawn at the onset of testing to test for interferents and subsequent samples of 1 mL each were taken at the following time-points: 0.5 h, 1 h, 2 h, 5 h, 8 h, and 24 h. These samples were analyzed via UV-Vis spectroscopy (Tecan m200 Infinity Multi-Well Plate Reader) for absorbance at 246 nM and were blanked relative to that of the empty vehicle.

Materials: 4-acetoxyacetanilide (Pro-APAP), Formulation Solvent: 50% DMSO in Polyethylene Glycol 400, and Receptor Media: 50% Ethanol in Polyethylene Glycol 400 at 37° C. Excised human skin information is shown in Table 1 and Franz cell parameters are shown in Table 2.

TABLE 1 characteristics of excised human skin

| | |
|---|---|
| Patient age: 52 years. | Thickness: Dermatomed (0.012-0.016 inches) |
| Race: Caucasian. | Resistance: All greater than 10k ohms. |
| Gender: Male. | |
| Location: Lumbar. | |

TABLE 2

Franz Cell Parameters

| | |
|---|---|
| Area of Diffusion: 0.64 cm$^2$/Franz Cell | Temperature: 37° C. |
| Receptor Volume: 5 mL | Approximately: 500-600 rpms |
| | Stir Bar Dimensions: 9 mm × 3 mm |

Figure 2:
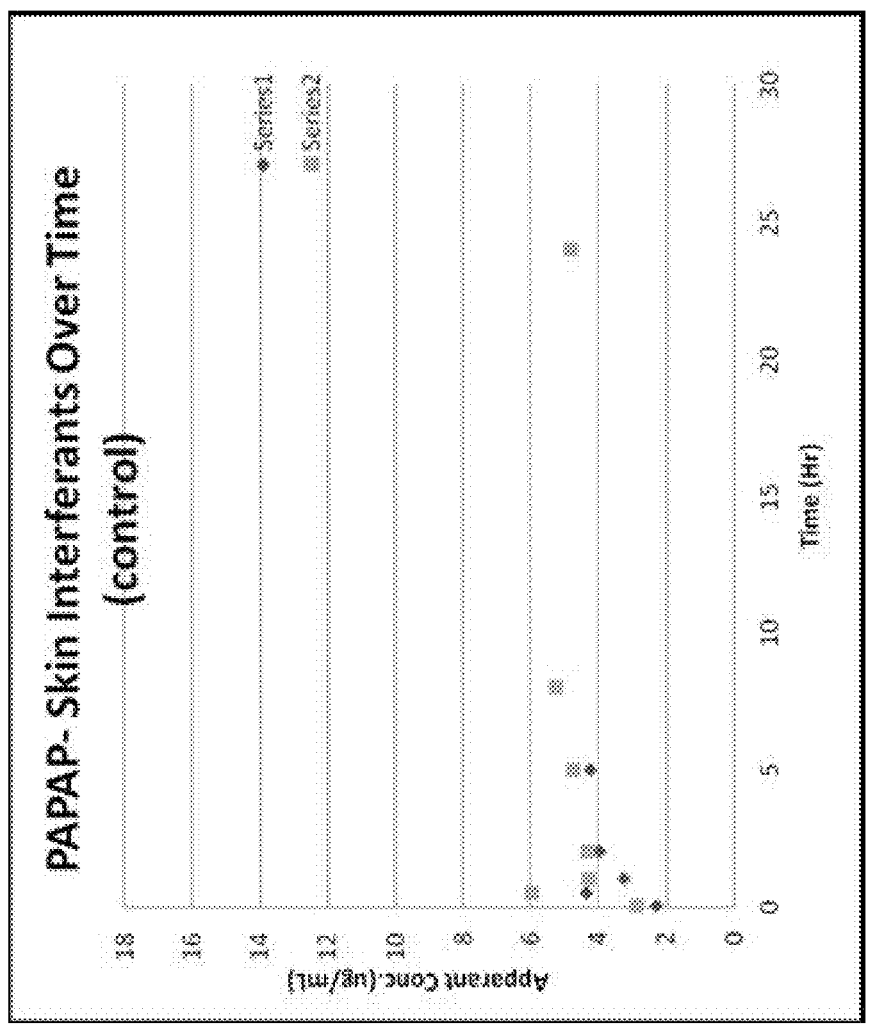
FIG. 2 shows the apparent concentration over time of potentially interfering compounds released from the human skin sample that absorb at 246 nm.

Results and Discussion: Screening or assaying for permeation through human skin can often be challenging due to the presence of interfering compounds that can leach from the skin into the receptor media. Initial testing was performed to see whether interfering compounds were extracted to a noticeable degree in the blank media. FIG. 2 shows the apparent concentration of interferents that appeared in the blank sample (i.e., in absence of drug). This method was used to create a baseline reading of UV absorbance, or "blank" to assess the amount of the active compound that permeates above and beyond this level. The plot in FIG. 2 shows that there is a small amount of interfering content that diffuses from the skin into the receptor solution. However this amount is very small (4 µg/mL) and remains constant throughout time, and therefore active samples can be adequately blanked with this data.

Figure 3:
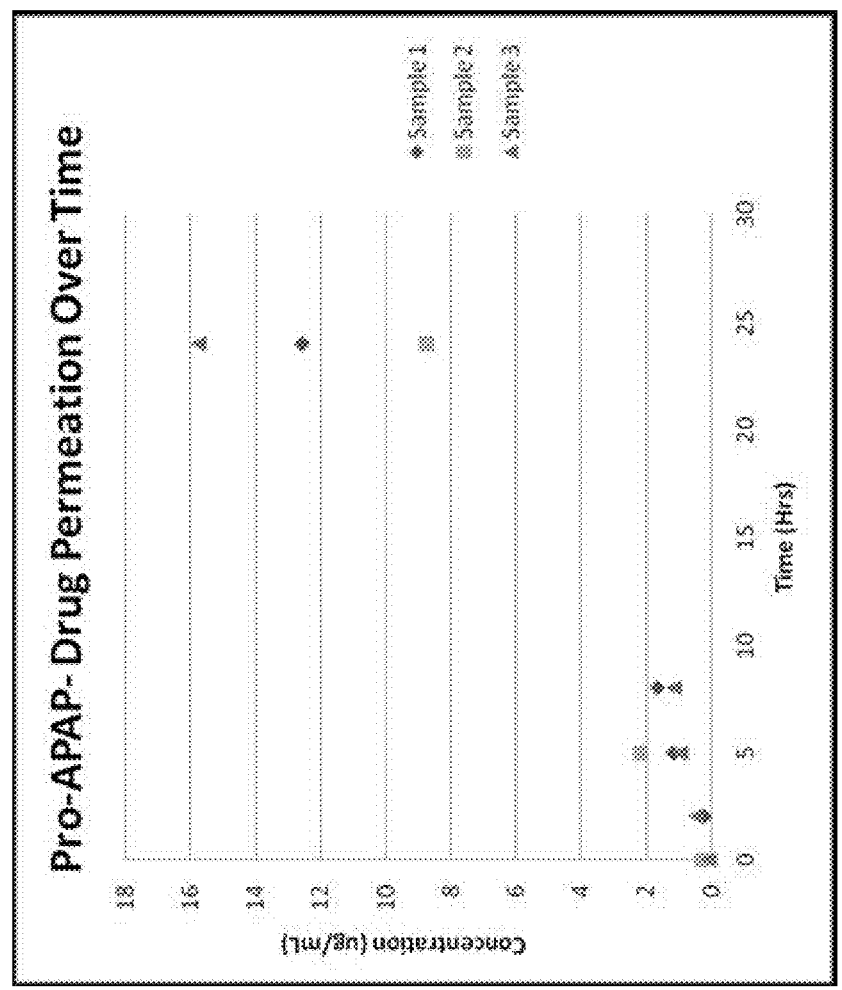
FIG. 3 shows the skin permeation of 4-acetoxyacetanilide by measuring the concentration of 4-acetoxyacetanilide in receptor media over time.

The concentration of the Pro-APAP compound, 4-acetoxyacetanilide, in the receptor media over time was also assessed. FIG. 3 shows the analysis of Pro-APAP concentration in receptor media over time. After subtracting the blank, the initial time points of 0 h, 0.5 h, and 2 h showed a very small concentration of the Pro-APAP in the receptor media. Beginning at the 5 h time point, the levels began to rise. The 8 h time point was roughly constant as compared to the 5 h time point. It is important to understand that because a sample was being extracted at each time point, a constant level corresponds to an increase in release of compound because the receptor media is subsequently diluted at each time point. The final time point at 24 h shows a very large increase in concentration of Pro-APAP (an average of 12.36 µg/mL, with a minimum of 8.76 µg/mL and a maximum of 15.78 µg/mL).

Figure 4:
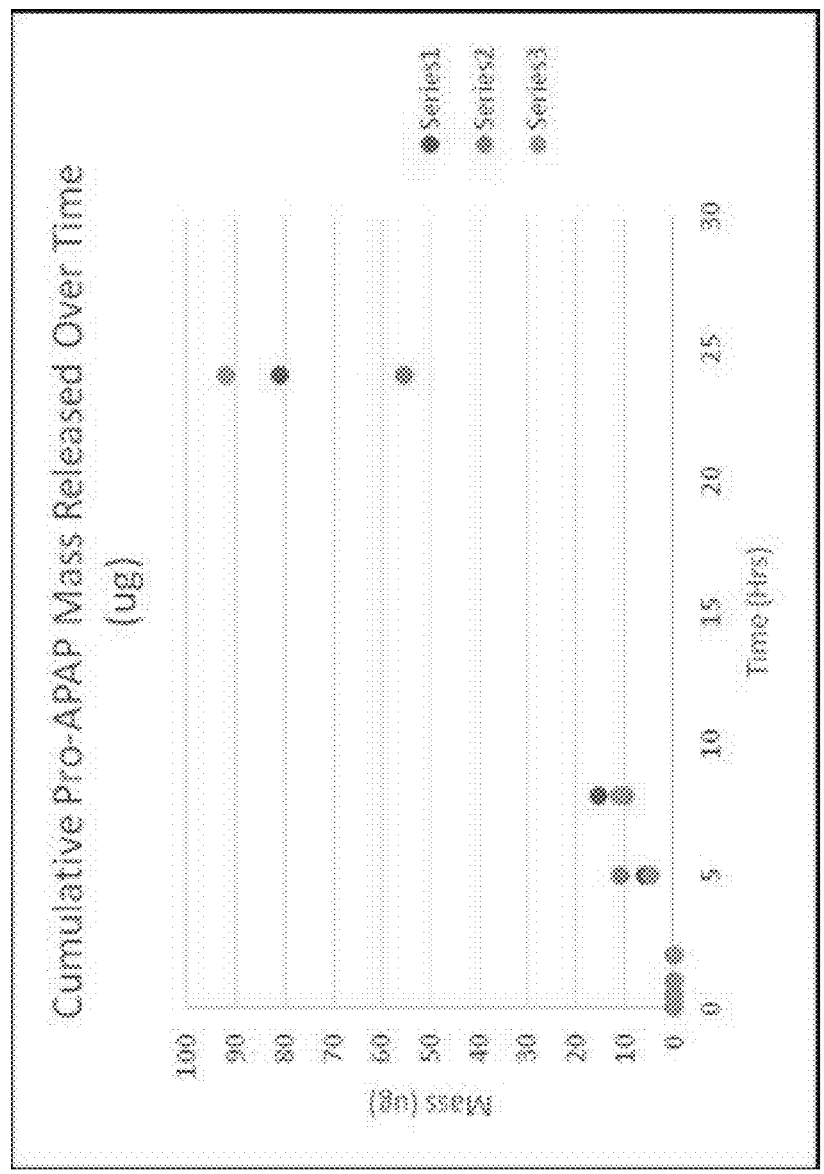
FIG. 4 shows the skin permeation of 4-acetoxyacetanilide by measuring the cumulative mass of 4-acetoxyacetanilide released over time into the receptor media.

Due to the dilution effect mentioned above, it is also important to assess the cumulative mass that is released over time. This can be useful for assessing the total delivered dose and it also corrects for the amount of compound that is lost through sampling (see FIG. 4). The initial time points were negligible relative to the blank or controls. At the 5 h time point, an average of 7.15 µg of Pro-APAP was released, with a minimum of 4.73 µg and a maximum of 10.8 µg. The last time point at 24 h had an average release of 76.15 µg of Pro-APAP, with a minimum of 55.45 µg and a maximum of 91.94 µg. These results are summarized in Table 3 below. The permeability coefficient range for 4-acetoxyacetanilide, was calculated to be 3.61-5.98 µg/h/cm$^2$ and the compound permeated to a total cumulative amount of around 80 µg per 0.66 cm$^2$.

TABLE 3

| Timepoint | Average Mass Released (µg) | Minimum (µg) | Maximum (µg) |
|---|---|---|---|
| 5 Hr | 7.16 | 4.73 | 10.88 |
| 8 Hr | 12.20 | 10.04 | 15.34 |
| 24 Hr | 76.16 | 55.45 | 91.95 |

These results demonstrate that the exemplary acetaminophen prodrug (Pro-APAP), 4-acetoxyacetanilide, successfully permeated through human skin when incorporated into the test transdermal system described herein.

Example 2

The purpose of this example was to study the stability, solubility, and skin permeation characteristics of an exemplary ibuprofen prodrug (Pro-IBU), ethyl 2-(4-isobutylphenyl)-propanoate, to determine its potential for transdermal delivery. Ethyl 2-(4-isobutylphenyl)-propanoate (CAS Number: 41283-72-1) has a molecular weight of 234.3 g/mol and a melting point of <102° C., and is soluble in DMSO and ethanol.

Ethyl 2-(4-isobutylphenyl)-propanoate was assessed for its ability to be soluble in high concentrations in a model solvent/vehicle that can be used in a transdermal device/patch system and achieve therapeutic drug dosage levels. The ability of the compound to remain stable in the solvent/vehicle was also tested.

Figure 5:
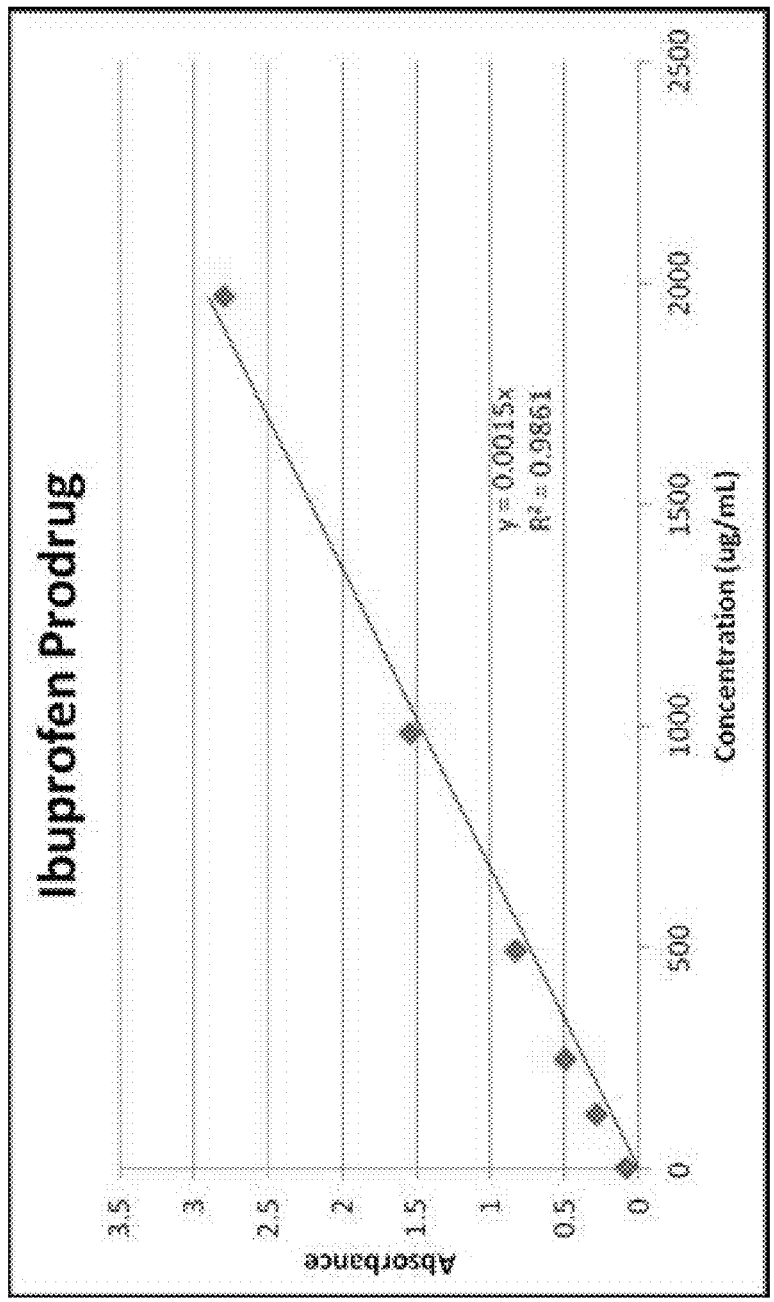
FIG. 5 shows the calibration of a UV-Vis spectrometer for use in determining the concentration of ethyl 2-(4-isobutylphenyl)-propanoate by detecting absorbance at 256 nm.

First, a suitable assay for detecting ethyl 2-(4-isobutylphenyl)-propanoate was developed. FIG. 5 shows the calibration of an ultraviolet/visible (UV-Vis) spectrometer (Tecan m200 Infinity Multi-Well Plate Reader) for use in determining the concentration of ethyl 2-(4-isobutylphenyl)-propanoate by detecting absorbance at 256 nm. Ethanol was used as the calibration standard diluent. Second, after screening several blends and co-solvents, a formulation comprising 50% DMSO in Polyethylene Glycol 400 was selected as the model solvent/vehicle for further testing. The pro-IBU compound, ethyl 2-(4-isobutylphenyl)-propanoate, was visually screened for physical and chemical stability over a 4-week period.

Skin permeation studies: Upon completion of the solubility and stability studies, the ability of the pro-IBU compound to permeate the skin in the selected solvent/vehicle was tested and the rate of permeation was measured to determine whether the compound will permeate to an extent relevant for clinical use in a transdermal patch. Specifically, ethyl 2-(4-isobutylphenyl)-propanoate was assessed for skin permeation across human skin over a 24 h time period.

Methods: For the skin permeation studies, a sample chamber containing 5 mL of 50% Polyethylene glycol 400 in ethanol was used as the receptor media. An initial sample of receptor media was drawn at the onset of testing to test for interferents and subsequent samples of 1 mL each were taken at the following time-points: 0.5 h, 1 h, 2 h, 5 h, 8 h, and 24 h. These samples were analyzed via UV-Vis spectroscopy (Tecan m200 Infinity Multi-Well Plate Reader) for absorbance at 246 nM and were blanked relative to that of the empty vehicle.

Materials: ethyl 2-(4-isobutylphenyl)-propanoate (pro-IBU), Formulation Solvent: 50% DMSO in Polyethylene Glycol 400, Receptor Media: 50% Ethanol in Polyethylene Glycol 400 at 37° C. Excised human skin information is shown in Table 4 and Franz cell parameters are shown in Table 5.

TABLE 4 characteristics of excised human skin

| | |
|---|---|
| Patient age: 52 years. | Thickness: Dermatomed (0.012-0.016 inches) |
| Race: Caucasian. | Resistance: All greater than 10k ohms. |
| Gender: Male. | |
| Location: Lumbar. | |

TABLE 5

Franz Cell Parameters

| | |
|---|---|
| Area of Diffusion: 0.64 cm$^2$/ Franz Cell | Temperature: 37° C. |
| | Approximately: 500-600 rpms |
| Receptor Volume: 5 mL | Stir Bar Dimensions: 9 mm × 3 mm |

Figure 6:
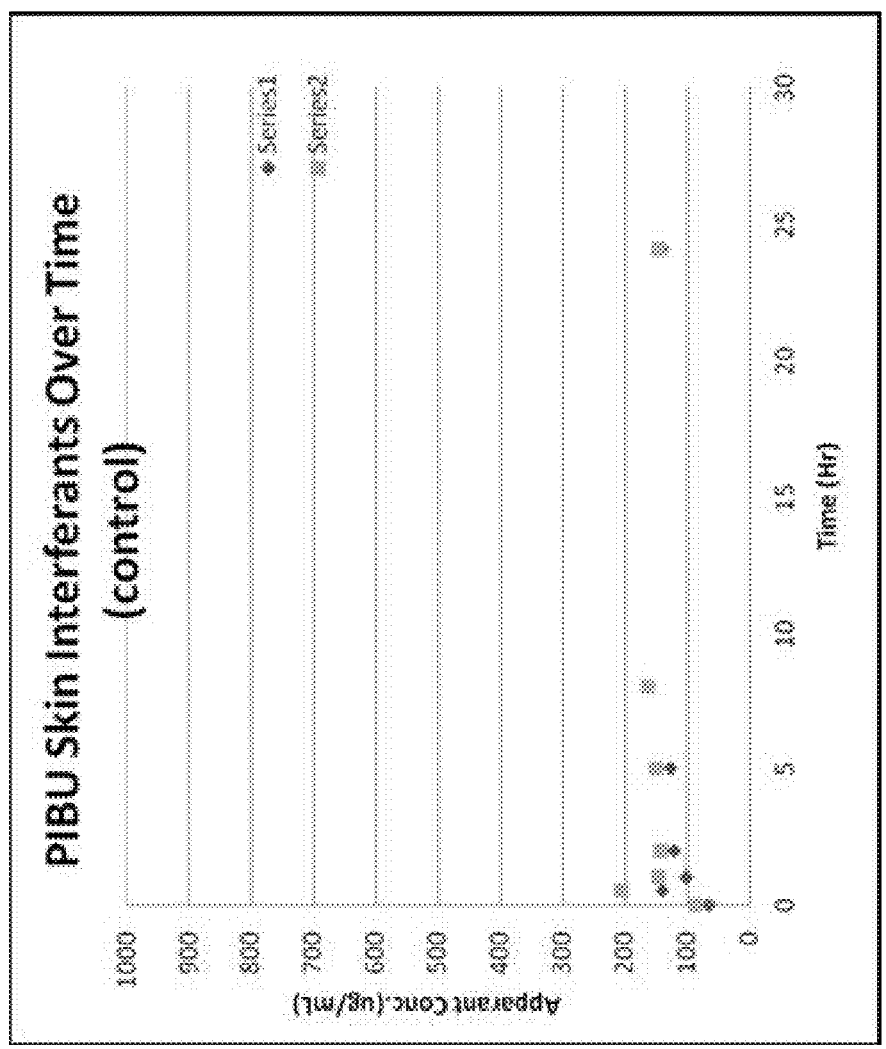
FIG. 6 shows the apparent concentration over time of potentially interfering compounds released from the human skin sample that absorb at 256 nm.

Results and Discussion: As described in Example 1, initial testing was performed to see whether interfering compounds that absorb at the same wavelength as the prodrug for ibuprofen (at 256 nm) were extracted to a noticeable degree in the blank media. The results were similar to that of the Pro-APAP assay in that material did appear to leach from the skin that does absorb in the range of 256 nm. However, the apparent concentration is much lower than that of what the Pro-IBU is expected to appear at, and therefore, it is relatively small in that regard. Therefore, these samples can serve as an adequate blank for adjusting the baseline level of absorbance observed in FIG. 6.

Figure 7:
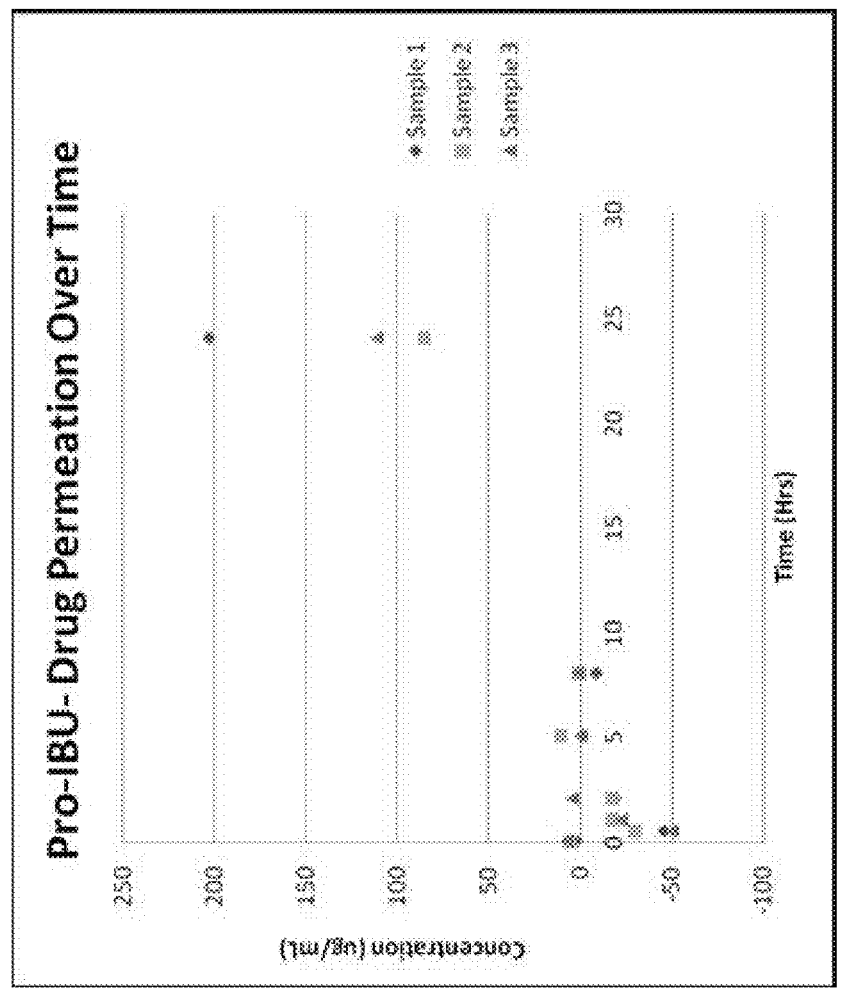
FIG. 7 shows the skin permeation of ethyl 2-(4-isobutylphenyl)-propanoate by measuring the concentration of ethyl 2-(4-isobutylphenyl)-propanoate in receptor media over time.

To assess the permeation over time of the Pro-IBU compound, ethyl 2-(4-isobutylphenyl)-propanoate, the concentration of the compound in the receptor media was measured over time (FIG. 7). Upon adjusting for and subtracting the blank samples, the very early time-points for the Pro-IBU compound appear to only have negligible concentrations of Pro-IBU on the receptor side of the skin. Essentially, in the first 2 hours of the study, the concentration was within the range of the background signal (i.e. noise) of the analytical method. The Pro-IBU compound emerges above the threshold for detection around 5 and 8 hrs, however these levels are relatively low. Interestingly, after the 8 h time point, the compound appeared to be rapidly released as the 24 h time-point showed a relatively high concentration of Pro-IBU in the receptor media (~200 µg/mL).

Figure 8:
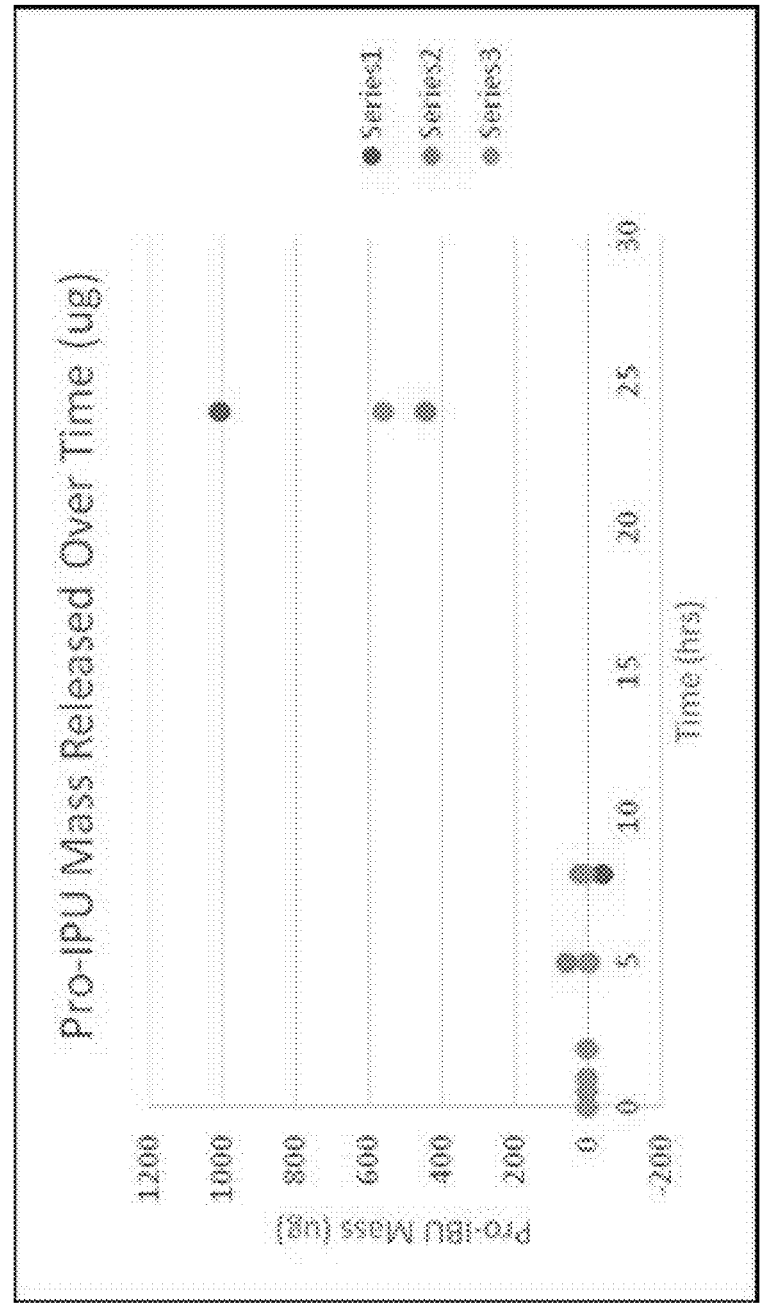
FIG. 8 shows the ethyl 2-(4-isobutylphenyl)-propanoate mass released into the receptor media over time.
Figure 9:
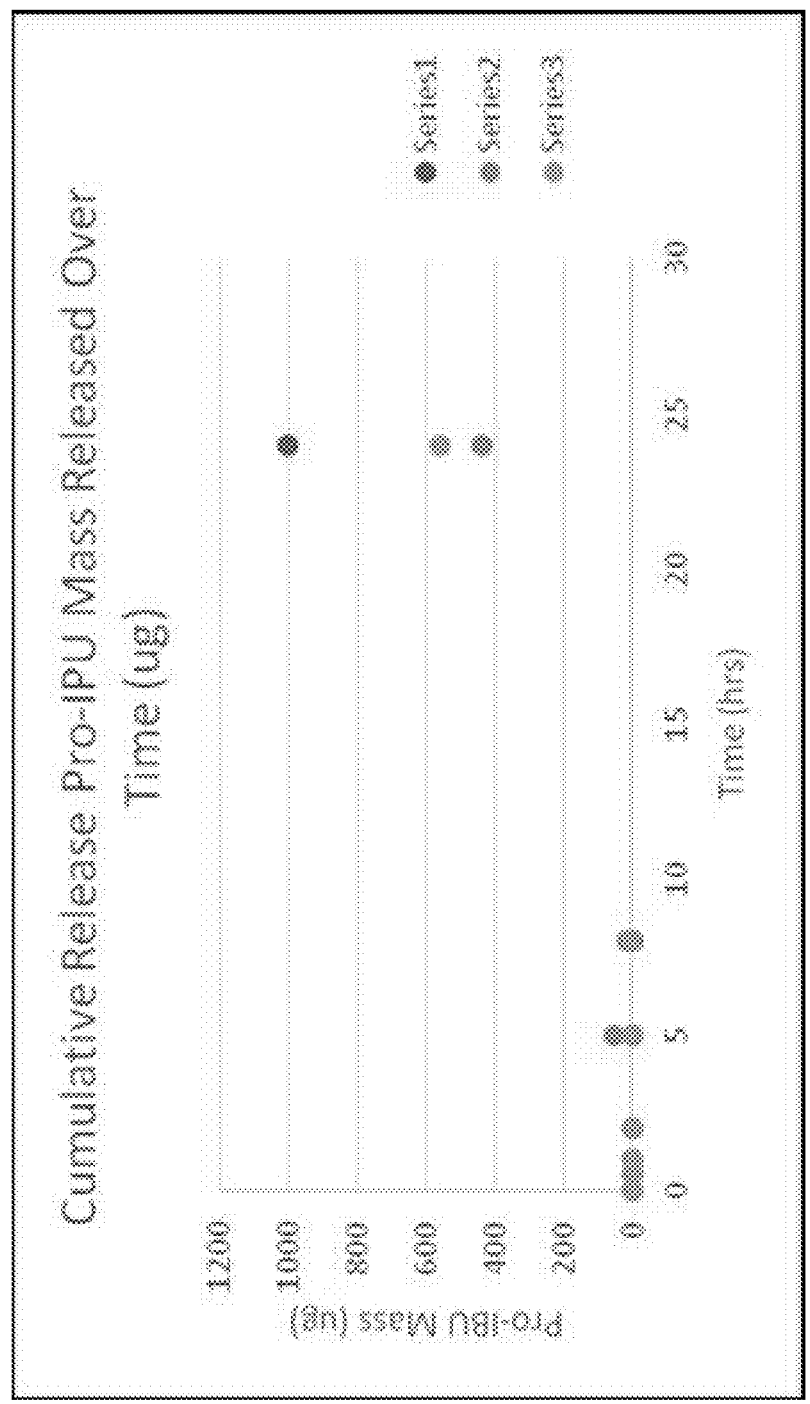
FIG. 9 shows the skin permeation of ethyl 2-(4-isobutylphenyl)-propanoate by measuring the cumulative mass of ethyl 2-(4-isobutylphenyl)-propanoate released over time into the receptor media. The values were adjusted for below baseline values.

Next, the total mass of Pro-IBU delivered across the skin was measured. FIG. 8 shows the Pro-IBU mass released over time and FIG. 9 shows the cumulative mass of Pro-IBU released over time. It should be noted that because there was very little Pro-IBU released during the early time points, the cumulative curves and the timecourse curves are very similar. Very little Pro-IBU was detectable by mass until the 5 h mark (FIGS. 8 and 9), when in one of the wells, 54 µg was detected. Then at the 8 h mark, two wells had detectable Pro-IBU, 70.8 µg and 5.66 µg. And finally, the 24 h time point showed a very large amount of the Pro-IBU compound in each of the wells. The 24 h mark had an average of 693 µg of pro-IBU, with a minimum of 511 µg and a maximum of 1,005 µg. This data is summarized in Table 6. The permeation coefficient of ethyl 2-(4-isobutylphenyl)-propanoate was calculated to be 33.32-65.47 µg/h/cm$^2$ and the compound permeated to a total cumulative amount of around 1,000 µg per 0.66 cm$^2$.

TABLE 6

| Timepoint | Average Mass Released (µg) | Minimum (µg) | Maximum (µg) |
|---|---|---|---|
| 5 Hr | 18.06 | 0.00 | 54.17 |
| 8 Hr | 25.50 | 0.00 | 70.83 |
| 24 Hr | 693.94 | 511.83 | 1005.67 |

In summary, it was found that both of the tested acetaminophen and ibuprofen prodrugs were detectable by UV-Vis spectroscopy and were characterized in the concentration range suitable for human skin permeation studies. It was also found that a suitable formulation vehicle could serve as a prototype for evaluating the permeation of each of the prodrug molecules through the skin. This information can be used to in transdermal patch systems for the delivery of prodrugs.

The permeation studies reveal that both the Pro-APAP and Pro-IBU permeate human skin over a 24 h period, although to different degrees and at different rates. The Pro-APAP compound was found to likely permeate faster. Both compounds had a lag time of between 2-5 hours. Pro-APAP permeated to a total cumulative amount of around 80 µg per 0.66 cm$^2$ as compared to around 1000 µg per 0.66 cm$^2$ for Pro-IBU. It will be understood by the skilled artisan that the rates and extent of absorption of the prodrugs from transdermal systems can be varied by employing additional dosage forms and/or formulations.

Example 3

This example illustrates the solubilities of APAP, IBU, Pro-APAP, and Pro-IBU in vehicle formulations F1 and F2.

Formulation F1 consisted of 50% Polyethylene Glycol (MW grade: 400) in 50% Ethanol. 50.2 mg of IBU was dissolved in 10.0 mL of F1, to produce a solution with a concentration of 5.02 mg/mL. IBU was soluble at this concentration.

501.84 mg of IBU was dissolved in 10.0 mL of F1 to produce a solution with a concentration of 50.184 mg/mL. This was the saturation point of IBU in F1.

245.8 mg of Pro-IBU was dissolved in 10.0 mL of F1 to produce a solution with a concentration of 24.9 mg/mL. Pro-IBU was freely soluble at this concentration.

127.688 mg of APAP was dissolved in 10.0 mL of F1 to produce a solution with a concentration of 12.8 mg/mL. This was the maximum solubility of APAP in F1.

250.822 mg of Pro-APAP was dissolved in 20.0 mL of F1 to produce a solution with a concentration of 12.5 mg/mL. This was the maximum solubility for Pro-APAP in F1.

A permeation enhanced vehicle formulation F3 was developed consisting of 33.3% dimethylsulfoxide (DMSO) and 66.6% ethanol. A solution of Pro-APAP in F3 was prepared by first dissolving 30.5 mg of Pro-APAP into 2 mL neat ethanol, and then slowly adding 1 mL DMSO to reach a 3 mL 10.1 mg/mL solution with a final DMSO concentration of 33.3%.

A solution of Pro-IBU in F3 was prepared by first dissolving 67.0 mg of Pro-IBU into 1 mL neat ethanol, and then slowly adding 0.50 mL DMSO to reach 1.5 mL of a 44.6 mg/mL solution with a final DMSO concentration of 33.3%.

Example 4

This example evaluated the stability of each of the prodrugs in vehicle F3.

A 50 mg/ml solution of Pro-APAP in F3 was prepared and monitored visually for three months to check for stability. Pro-APAP was determined to be stable in this solution for the duration of the experiment.

A 70 mg/ml solution of Pro-IBU in F3 was prepared and monitored visually for three months to check for stability. Pro-APAP was determined to be stable in this solution for the duration of the experiment.

Example 5

This example was undertaken to estimate the minimum threshold concentration for each of the prodrugs.

Transdermal drug delivery is based on simple diffusion and is a linear process. It follows that the following estimates can be made via extrapolation: (i) minimum Pro-APAP minimum range of about 2.5 mg/ml to about 5 mg/ml and similarly (ii) Pro-IBU minimum concentration range of about 10 mg/ml to about 20 mg/ml.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A transdermal drug delivery system for topical application to a subject in need, comprising:
   (a) an adhesive polymer matrix layer; and
   (b) an acetaminophen prodrug dispersed within the polymer matrix layer,
   wherein the polymer matrix layer comprises dimethylsulfoxide (DMSO) and polyethylene glycol 400 (PEG 400),
   wherein the acetaminophen prodrug is chemically and physically stable within the polymer matrix layer, and
   wherein upon topical application of the transdermal drug delivery system to the skin or mucosa of a subject in need:
      (i) the system releases a therapeutically effective amount of the prodrug over a period of time of about 5 hours to about 24 hours; and
      (ii) the acetaminophen prodrug diffuses through the skin or mucosa of the subject to achieve therapeutic systemic levels of the acetaminophen prodrug wherein, the transdermal drug delivery system is a transdermal patch and the acetaminophen prodrug has a the structure of formula I:

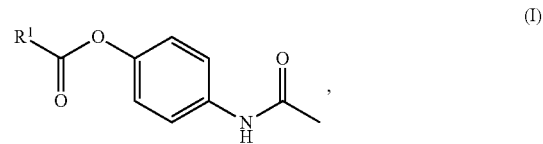

wherein $R^1$ is optionally substituted $C_1$-$C_6$ alkyl.

2. The transdermal drug delivery system of claim 1, wherein $R^1$ is methyl.

3. The transdermal drug delivery system of claim 1, wherein the acetaminophen prodrug is stable over a period of time of about 3 months to about 3 years.

4. The transdermal drug delivery system of claim 1, wherein the transdermal drug delivery system further comprises:
   (a) a backing layer;
   (b) a release liner;
   (c) a rate-controlling polymeric membrane; or
   (d) any combination of (a), (b), and (c).

5. The transdermal drug delivery system of claim 1, wherein the adhesive polymer matrix comprises:
   (a) a pressure-sensitive adhesive;
   (b) an acrylic polymer;
   (c) a polymer in which the acetaminophen prodrug is soluble; or
   (d) any combination of (a), (b) and/or (c).

6. The transdermal drug delivery system of claim 1, wherein the adhesive polymer matrix comprises from about 225 mg to about 2,500 mg of the acetaminophen prodrug.

7. The transdermal drug delivery system of claim 1, wherein the delivery system has a skin or mucosa contact region area of from about 1 cm² to about 20 cm².

* * * * *